United States Patent
Iizuka et al.

(10) Patent No.: US 8,393,217 B2
(45) Date of Patent: Mar. 12, 2013

(54) ULTRASONIC FLAW DETECTION APPARATUS AND ULTRASONIC FLAW DETECTION METHOD FOR PIPE

(75) Inventors: Yukinori Iizuka, Kawasaki (JP);
Kazuhito Kenmochi, Chiba (JP);
Hiroyasu Yokoyama, Handa (JP);
Tomohiro Inoue, Kawasaki (JP);
Shigeto Sakashita, Kawasaki (JP)

(73) Assignee: JFE Steel Corporation, Tokyo (JP)

( * ) Notice: Subject to any disclaimer, the term of this patent is extended or adjusted under 35 U.S.C. 154(b) by 457 days.

(21) Appl. No.: 12/449,744

(22) PCT Filed: May 18, 2007

(86) PCT No.: PCT/JP2007/060662
§ 371 (c)(1),
(2), (4) Date: Nov. 24, 2009

(87) PCT Pub. No.: WO2008/105111
PCT Pub. Date: Sep. 4, 2008

(65) Prior Publication Data
US 2010/0101326 A1    Apr. 29, 2010

(30) Foreign Application Priority Data
Feb. 28, 2007    (JP) .................. 2007-048875

(51) Int. Cl.
*G01N 29/04*    (2006.01)
(52) U.S. Cl. .......................... 73/588; 73/622
(58) Field of Classification Search .......... 73/588, 73/624, 628, 598–600, 602, 619–622, 625, 73/627, 618, 633
See application file for complete search history.

(56) References Cited

U.S. PATENT DOCUMENTS

| | | | | | |
|---|---|---|---|---|---|
| 4,305,297 | A | * | 12/1981 | Ries et al. | 73/628 |
| 4,458,534 | A | * | 7/1984 | Kising | 73/642 |
| 4,522,064 | A | * | 6/1985 | McMillan | 73/592 |

(Continued)

FOREIGN PATENT DOCUMENTS

| JP | A-60-205356 | 10/1985 |
|---|---|---|
| JP | A-61-111461 | 5/1986 |

(Continued)

OTHER PUBLICATIONS

"Ultrasonic flaw detection series (II) Ultrasonic flaw detection method for welded steel pipe", Iron and Steel Institute of Japan, pp. 28-31, 1988.

(Continued)

*Primary Examiner* — J M Saint Surin
(74) *Attorney, Agent, or Firm* — Oliff & Berridge, PLC

(57) ABSTRACT

The present invention has a structure capable of detecting the scattered-type penetrator having oxides each with the size of several μm sparsely and widely dispersed. Specifically, the structure includes a wave transmission unit 6 for transmitting an ultrasonic wave to the welded surface of the welded portion 2 in a pipe axial direction of the pipe 1 such that the beam width of a transmission beam 8 is brought into a range from 0.5 mm to 2.5 mm, and a wave reception unit 7 for receiving at least a portion of the reflection wave (reception beam 9) at the welded surface. The wave transmission unit 6 and the wave reception unit 7 include transmission/reception units formed of different groups of transducer elements on at least one or more array probes 5 arranged in the circumferential direction of the pipe.

23 Claims, 25 Drawing Sheets

U.S. PATENT DOCUMENTS

| | | | | |
|---|---|---|---|---|
| 4,524,622 A | * | 6/1985 | Suzuki et al. | 73/620 |
| 4,555,948 A | * | 12/1985 | Miyamoto et al. | 73/640 |
| 4,579,372 A | | 4/1986 | Morrill | 285/18 |
| 4,627,289 A | * | 12/1986 | Fukuda et al. | 73/622 |
| 4,712,722 A | * | 12/1987 | Hood et al. | 228/104 |
| 7,168,322 B2 | * | 1/2007 | Bardoux et al. | 73/588 |
| 7,698,944 B2 | * | 4/2010 | Takada | 73/588 |
| 7,762,137 B2 | * | 7/2010 | van der Ent et al. | 73/627 |
| 7,779,694 B2 | * | 8/2010 | Iizuka | 73/622 |
| 7,784,347 B2 | * | 8/2010 | Messer et al. | 73/618 |
| 7,874,212 B2 | * | 1/2011 | Yamano | 73/622 |

FOREIGN PATENT DOCUMENTS

| | | |
|---|---|---|
| JP | A-04-274756 | 9/1992 |
| JP | A-07-035729 | 2/1995 |
| JP | A-10-111281 | 4/1998 |
| JP | A-11-183446 | 7/1999 |
| JP | B2-3165888 | 3/2001 |
| JP | B2-3721827 | 9/2005 |
| JP | B2-3731369 | 10/2005 |
| JP | A-2007-163470 | 6/2007 |

OTHER PUBLICATIONS

International Search Report issued on Jul. 27, 2007 in International Application No. PCT/JP2007/060662.

International Preliminary Report on Patentability dated Sep. 1, 2009 issued in PCT/JP2007/060662 (witb translation).

* cited by examiner

STEP 1: INNER SURFACE SIDE OF FOCUS POSITION, START OF SCAN

STEP 2: SCAN TOWARD OUTER SURFACE SIDE OF FOCUS POSITION

STEP 3: SCAN TOWARD OUTER SURFACE SIDE OF FOCUS POSITION

STEP 4: OUTER SURFACE SIDE OF FOCUS POSITION, END OF SCAN

| SCANNING LINE | TRANSDUCER ELEMENT NO. | NUMBER OF TRANSDUCER ELEMENTS | DEFLECTION ANGLE | FOCUS DISTANCE |
|---|---|---|---|---|
| A | 17-22 | 6 | -6.0° | 31.7 mm |
| B | 71-90 | 20 | 0 | 103 mm |
| C | 124-155 | 32 | -6.0° | 177 mm |

C-SCAN RESULTS AT 50MHz WITH BEAM DIAMTER OF 100 μm
FIG. 17A  C-SCAN DATA OF SAMPLE A
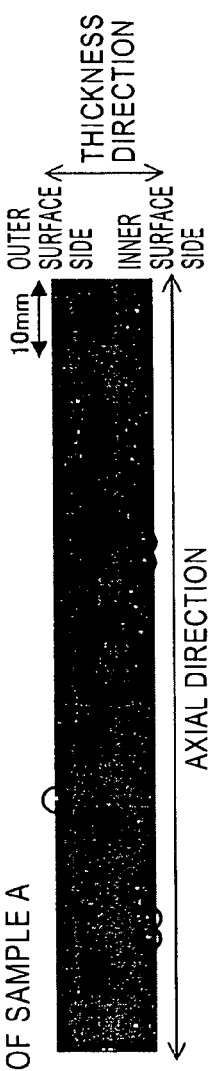
FIG. 17B  SIGNAL INTENSITY DISTRIBUTION OF SAMPLE A
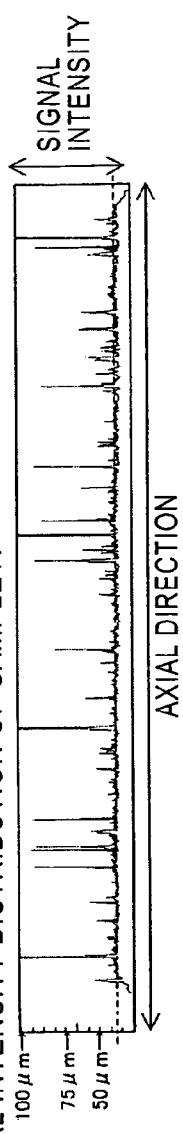
FIG. 17C  C-SCAN DATA OF SAMPLE B
FIG. 17D  SIGNAL INTENSITY DISTRIBUTION OF SAMPLE B
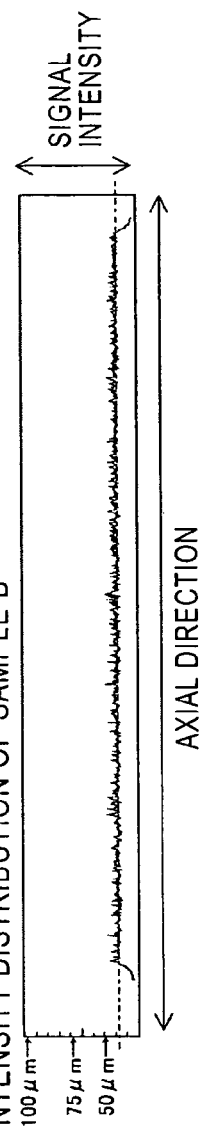

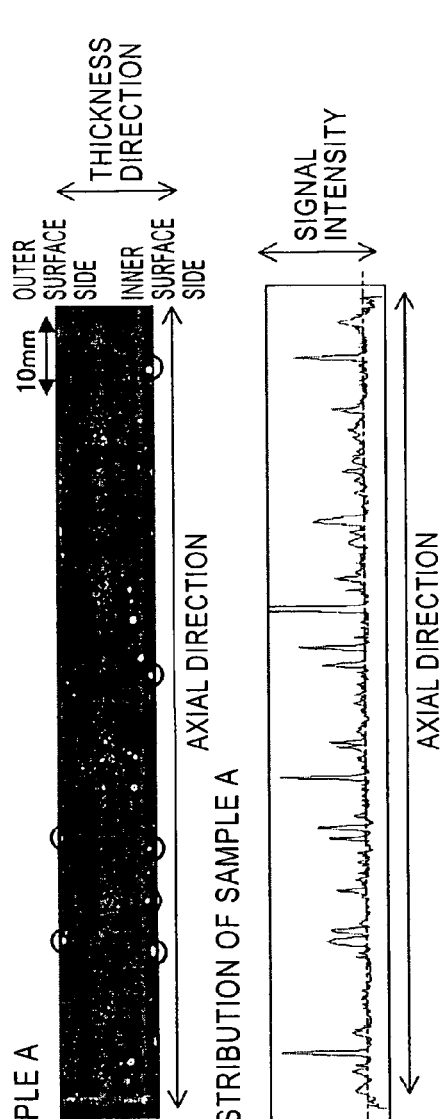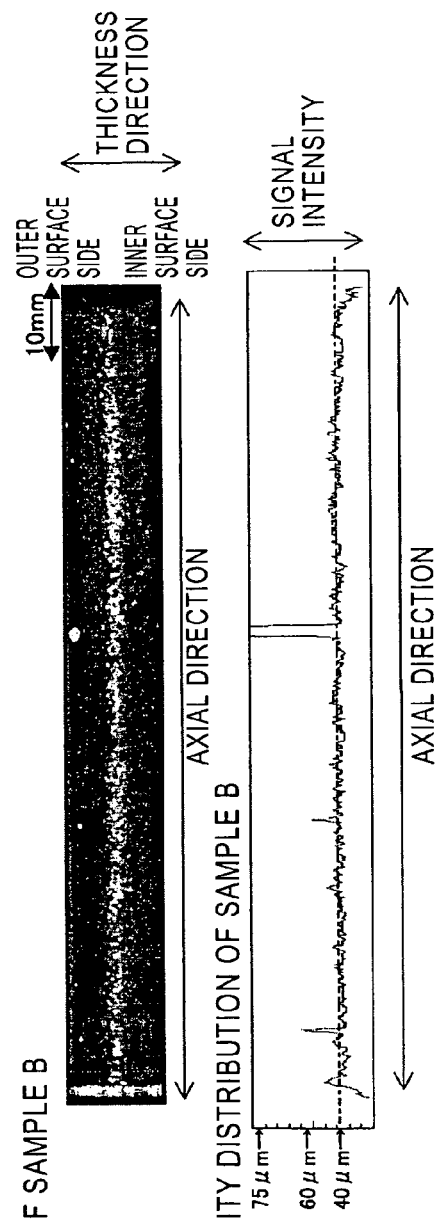
FIG. 18A C-SCAN DATA OF SAMPLE A
FIG. 18B SIGNAL INTENSITY DISTRIBUTION OF SAMPLE A
FIG. 18C C-SCAN DATA OF SAMPLE B
FIG. 18D SIGNAL INTENSITY DISTRIBUTION OF SAMPLE B

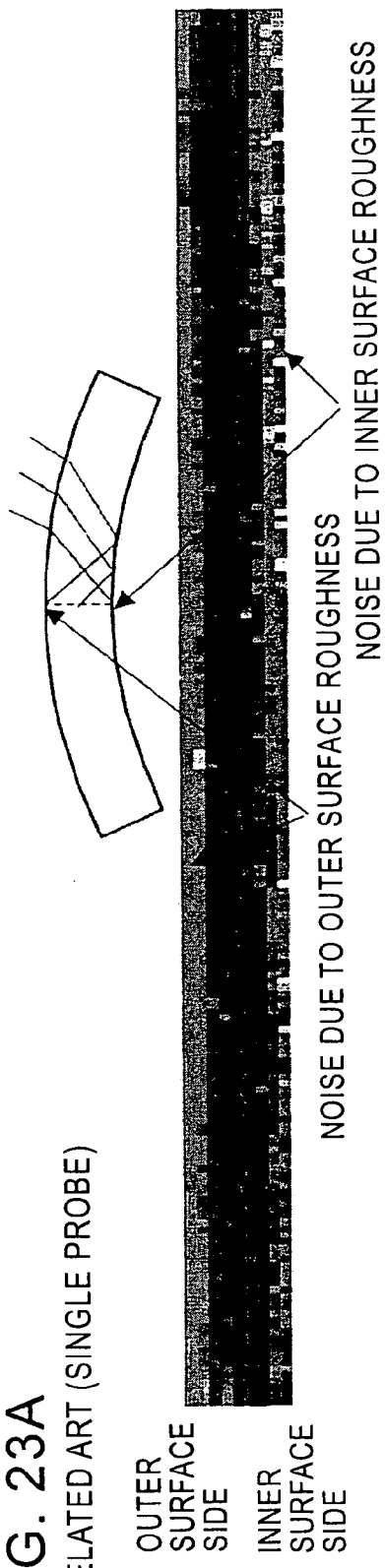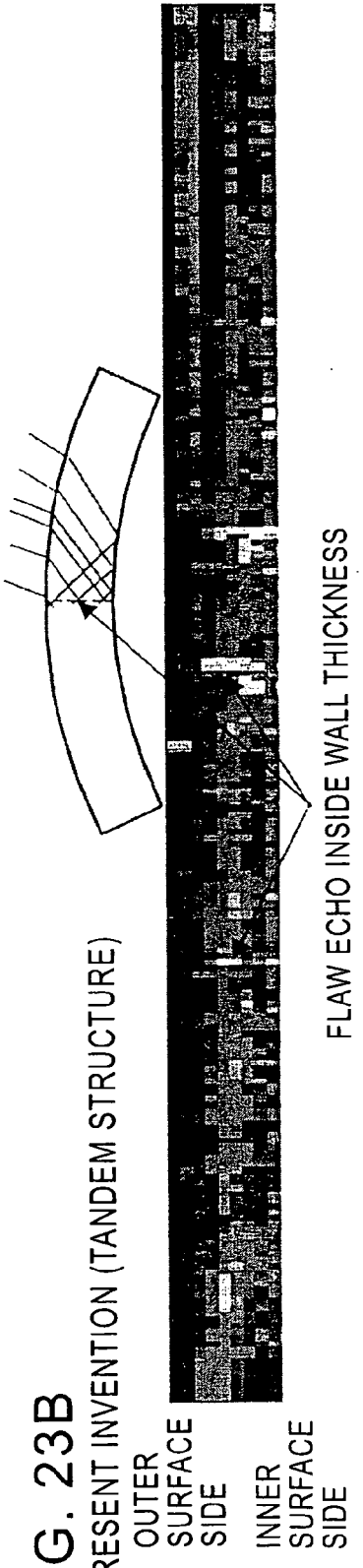
FIG. 23A RELATED ART (SINGLE PROBE)
FIG. 23B PRESENT INVENTION (TANDEM STRUCTURE)

$\theta a = 90 - \theta$
$\theta b = \theta$ (b) LATERAL WAVE → LATERAL WAVE $\theta a = 90 - \theta - \theta 1$
$\theta b = \theta + \theta 2$

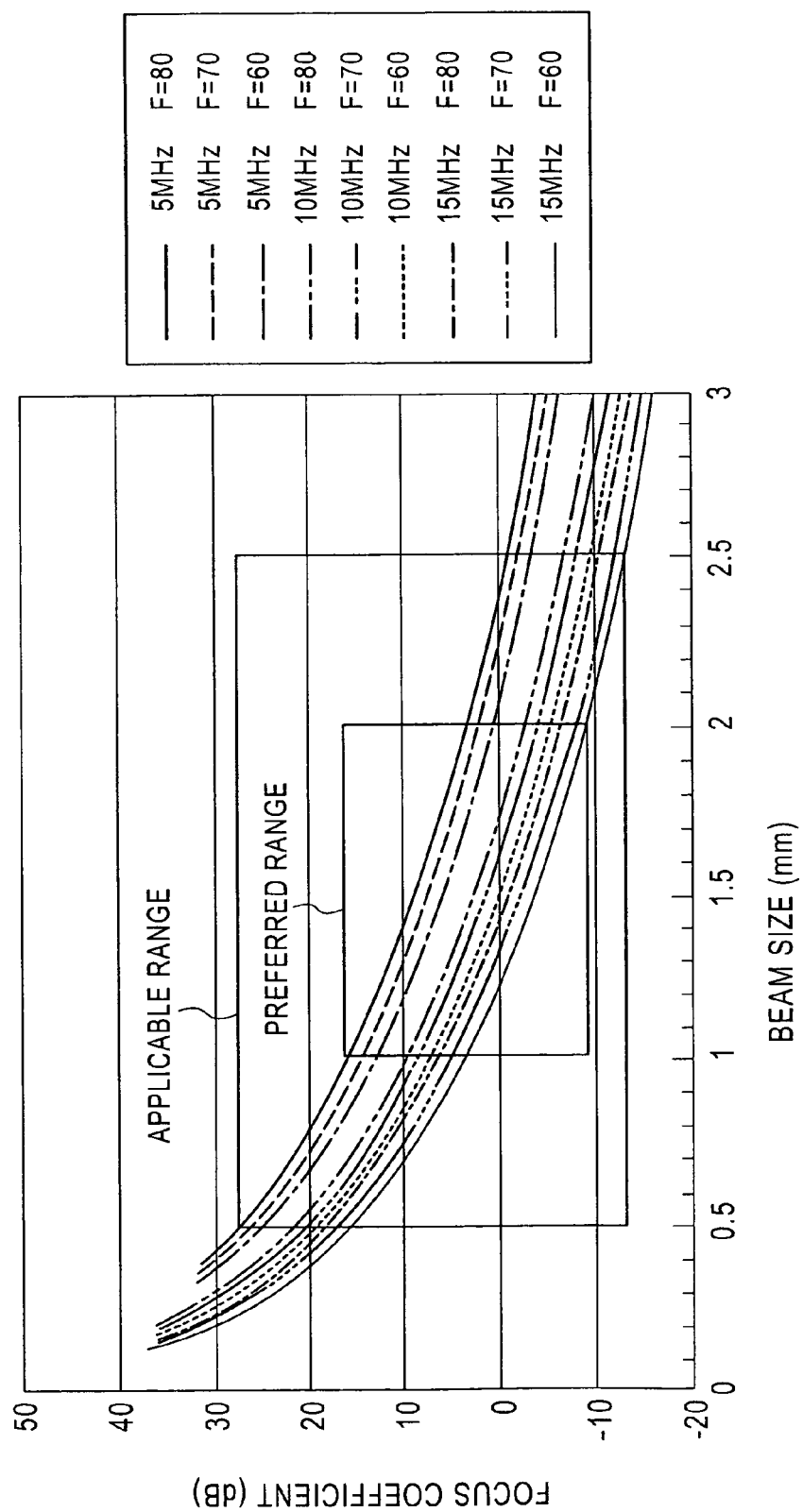

ULTRASONIC FLAW DETECTION APPARATUS AND ULTRASONIC FLAW DETECTION METHOD FOR PIPE

TECHNICAL FIELD

The present invention relates to an ultrasonic flaw detection apparatus and an ultrasonic flaw detection method for a pipe for accurately detecting a minute flaw generated in a welded portion of a welded steel pipe by conducting the ultrasonic flaw detection.

BACKGROUND ART

In a welded steel pipe, the quality of a welded portion is very important, and on-line flaw testing of the welded portion is ordinarily carried out by angle beam testing in a manufacturing process. In the technique, an ultrasonic wave is obliquely incident on an inspection surface of the sample to detect the flaw on the inner/outer surfaces of the sample, and the flaw inside the sample based on the reflected wave from the flaw. Ordinarily, a reflection technique method using an ultrasonic beam of 5 MHz having a refraction angle of 45° is applied to, for example, a electric resistance welded pipe, and flaws of the order of millimeters, for example, incomplete penetrations, burn through, and cracks due to inclusion, and the like are detected.

In contrast, recently, since very severe quality is required to the welded steel pipe, it is required to detect flaws smaller than conventional ones. For example, it is required to detect cold joint flaws and minute penetrators in a electric resistance welded pipe and to detect blow holes and the like in a laser welded pipe, and these flaws have a very small size of several tens to several hundreds of micron meters. Further, as a position of occurrence of flaws, they may occur in any location from an inside surface to an outside surface along a welding line. The incident point of the ultrasonic beam may be different from the return point depending on the flaw position. Since flaws are not detected often by ultrasonic flaw detection technique used practically up to now due to influence of them, a technique capable of detecting flaw more accurately is required.

The following conventional techniques are disclosed as techniques of detecting the minute flaw in the welded steel pipe.

Japanese Unexamined Patent Application Publication No. 60-205356 improves a penetrator detection capability in an angle beam testing by using a point focus type probe having a frequency of 8 MHz or higher.

Further, Japanese Unexamined Patent Application Publication No. 11-183446 improves a detection capability by forming a focus beam by an array probe so that blow holes can be detected by scanning from the inside surface to the outside surface of a welded portion by a sector scan.

Further, Japanese Unexamined Patent Application Publication No. 61-111461 detects cold joint flaws, which are mixed as a group of minute FeO of several micron meters or less, by causing an ultrasonic wave to be incident on a welded portion from the outside surface of a pipe at incident angle from 0° or more to 20° or less while setting the frequency of the ultrasonic wave from 25 MHz or more to 500 MHz or less.

Further, Japanese Unexamined Patent Application Publication No. 7-35729 detects blow holes of 0.1 mm or more using a plurality of point focus type probes, which have a frequency of from 20 MHz to 80 MHz and are disposed such that a focus position has a pitch of 3 mm or less from just above a seam.

It is noted that the description will refer to Japanese Unexamined Patent Application Publication No. 4-274756 and the document titled "Ultrasonic flaw detection series (II) Ultrasonic flaw detection method for welded steel pipe", edited by Iron and Steel Institute of Japan, pp. 28-31, 1988.

However, the problems described below still remain even in the techniques disclosed above.

First, Japanese Unexamined Patent Application Publication No. 60-205356 has a problem in that many channels are necessary to detect the flaws in entire area in the depth direction of a welded portion (wall thickness direction of the steel pipe) without omitting them because the beam width of the focused ultrasonic wave is narrow and thus an equipment cost become expensive and further in that when a pipe size is changed, a position adjustment and the like are troublesome. Further, when a flaw is not a blow hole shape and is a plane shape as that in a penetrator and a cold joint as well as a flaw is located in a wall thickness inside portion, it is difficult to detect the flaw because the reflection wave travels in a direction different from the incident direction.

Further, in Japanese Unexamined Patent Application Publication No. 11-183446, since only one array probe is necessary as well as the setting can be electronically carried out when a size is changed, it can overcome the former problem shown in Japanese Unexamined Patent Application publication No. 60-205356. However, the latter problem is still remains unsolved.

Further, when a flaw shape is a plane shape as described above, since an upset is applied to a seam portion, in, for example, a electric resistance welded pipe, a flaw has a very narrow width of 100 μm or less when viewed from just above the seam. Accordingly, the reflection wave from the flaw is actually very weak even in the techniques of Patent Documents 3 and 4, and thus it is often difficult to detect the flaw. Further, since an area of about 1 to 2 mm in the vicinity of a surface echo is made to a dead zone owing to reverberation of the surface echo, a problem arises in that when a flaw is located in the vicinity of an outside surface, it cannot be detected.

As described above, a technique for detecting the minute flaws of about several hundreds of micron meters or less, which occur in a welded portion of a welded steel pipe in a pipe-axial direction, nondestructively, accurately, stably, and online, is not established except a C-scan technique for detecting it off-line by a sample cut out from the welded portion.

DISCLOSURE OF INVENTION

An object of the present invention, which was made in view of the above circumstances, is to provide an apparatus and a method for performing the accurate detection of the minute flaw inside the wall thickness of the welded portion of the seam-welded pipe, which may influence the mechanical characteristics.

The following means may be provided for the purpose of solving the aforementioned problems.

[1]. An ultrasonic flaw detection apparatus for a pipe according to the present invention includes:

a wave transmission unit for transmitting an ultrasonic wave to a welded surface of a welded portion of the pipe in a pipe axial direction so that a beam width is within a range from 0.5 mm to 2.5 mm; and a wave reception unit for receiving partly or entirely a reflection wave reflected at the welded surface, wherein the wave transmission unit and the wave reception unit are provided with transmission/reception units comprising different groups of transducer elements on at least one array probe arranged in a circumferential direction of the pipe.

[2]. The ultrasonic flaw detection apparatus for a pipe according to [1] may further includes a control unit for controlling an aperture width of the ultrasonic wave for transmission such that the beam width of an ultrasonic beam to the welded surface is held in the range.

[3]. In the ultrasonic flaw detection apparatus for a pipe according to [2], the control unit may control the aperture width of the ultrasonic wave by a number of transducer elements to be simultaneously excited.

[4]. In the ultrasonic flaw detection apparatus for a pipe according to any one of [1] to [3], the wave transmission unit may transmit the ultrasonic wave having a focusing coefficient of from −13 dB to 28 dB, the focusing coefficient indicating increase in an acoustic pressure at a focus position.

[5]. In the ultrasonic flaw detection apparatus for a pipe according to any one of [2] to [4], the wave transmission unit may transmit the ultrasonic waves to the welded surface of the welded portion of the pipe in the pipe axial direction and an inner surface of the pipe so that the ultrasonic wave is incident at an angle ranging from 33.2° to 56.8°, respectively;

the wave reception unit may receive partly or entirely the reflection wave in a direction within a range from −12° to 16° with respect to a mirror reflection direction on the welded surface; and the control unit may scan the pipe in a thickness direction by carrying out a control to change the group of transducer elements corresponding to the wave transmission unit and the wave reception unit on the array probe or to change an angle of the array probe, and controlling an incident angle of the ultrasonic wave to the pipe in the respective transmitting wave and receiving waves so that the angles of incidence to the welded surface and the inner surface and the angle of the reflection wave on the welded surface are kept within the ranges as to the transmitted wave and the received wave, respectively.

[6]. In the ultrasonic flaw detection apparatus for a pipe according to [5], the control unit may control the incident angle and the focus position to the pipe by shifting a timing for the wave transmission and/or the wave reception with respect to each of the transducer elements in the group of transducer elements so that the incident angle to the welded surface and the inner surface, and the angle of the reflecting wave on the welded surface are kept within the defined ranges, respectively.

[7]. In the ultrasonic flaw detection apparatus for a pipe according to [5] or [6], the incident angle of at least one of the ultrasonic wave at the transmission side and the ultrasonic wave at the reception side to the pipe may be kept to a predetermined angle.

[8]. In ultrasonic flaw detection apparatus for a pipe according to any one of [5] to [7], the control unit may control at least one of the wave transmission and the wave reception with respect to the respective transducer elements so that the incident angle of the ultrasonic wave to the pipe is made to a predetermined angle.

[9]. In the ultrasonic flaw detection apparatus for a pipe according to any one of [1] to [8], the array probe may have the group of transducer elements with a curvature so that they are disposed along the circumferential direction of the pipe.

[10]. In the ultrasonic flaw detection apparatus for a pipe according to any one of [1] to [9], the array probe may include an acoustic lens for focusing the wave transmission beam and the wave reception beam to the pipe axial direction of the pipe, and a focus distance of the acoustic lens may be set shorter as it is nearer to the welded portion and longer as it is farther from the welded portion.

[11]. In the ultrasonic flaw detection apparatus for a pipe according to any one of [1] to [10], the transmission/reception unit may comprise a plural array probes as well as includes a wave transmission unit and a wave reception unit on each array probes.

[12]. In the ultrasonic flaw detection apparatus for a pipe according to any one of [1] to [10], the transmission unit and the reception unit of the transmission/reception unit may comprise different array probes.

[13]. In the ultrasonic flaw detection apparatus for a pipe according to any one of [5] to [10], the transmission unit and the reception unit of the transmission/reception unit may comprise different array probes; and the control unit may change deflection angles of the wave transmission beam and the wave reception beam from the respective array probes.

[14]. In the ultrasonic flaw detection apparatus for a pipe according to any one of [5] to [13], the control unit may change the incident angle and the focus position of the ultrasonic wave to the pipe upon the wave transmission and/or the wave reception so that scanning lines of the wave transmission beam intersect the wave reception beam at a plurality of positions in the circumferential direction of the pipe.

[15]. In an ultrasonic flaw detection method for a pipe, the ultrasonic flaw detection method uses an ultrasonic flaw detection apparatus for a pipe comprising a wave transmission unit and a wave reception unit composed of different groups of transducer elements on at least one array probe arranged in a circumferential direction of the pipe, the ultrasonic wave is transmitted to a welded surface of a welded portion of the pipe in an axial direction such that a beam width is within a range from 0.5 mm to 2.5 mm.

[16]. In the ultrasonic flaw detection method for a pipe according to [15], an aperture of the ultrasonic wave used for the wave transmission may be controlled such that the beam width of the ultrasonic beam to the welded surface is kept in the range.

[17]. In the ultrasonic flaw detection method for a pipe according to [16], the aperture of the ultrasonic wave may be controlled by a number of the transducer elements in the group of transducer elements to be simultaneously excited.

[18]. In the ultrasonic flaw detection method for a pipe according to any one of [15] to [17], the ultrasonic wave having a focussing coefficient of from −13 dB to 28 dB may be transmitted, the focussing coefficient indicating an increase in an acoustic pressure at a focus position.

[19]. In the ultrasonic flaw detection method for a pipe according to any one of [15] to [18], the ultrasonic wave may be transmitted from the wave transmission unit to the welded surface of the welded portion of the pipe in the pipe axial direction and an inner surface of the pipe so that incident angles are within a range from 33.2° to 56.8°, respectively;

at least a portion of a reflection wave reflected to a direction in a mirror reflection direction on the welded surface in a range from −12° to 16° may be received by the wave reception unit: and a scanning may be performed in a direction of a thickness of the pipe under the control for changing the group of transducer elements corresponding to the wave transmission unit and the wave reception unit on the array probe or changing an angle of the array probe.

[20]. In the ultrasonic flaw detection method for a pipe according to any one of [15] to [19], the incident angle to the pipe and the focus position may be controlled by shifting a timing for the wave transmission and/or wave reception for the respective transducer elements in the group of transducer elements.

[21]. In the ultrasonic flaw detection method for a pipe according to any one of [15] to [20], the incident angle of at least one of the ultrasonic wave at the wave transmission side and the ultrasonic wave at the wave reception side with respect to the pipe may be kept to a predetermined angle.

The focus position of the wave transmission beam is not necessarily the same as the focus position of the wave reception beam. They may be in the respective ranges corresponding to each beam width at which the wave transmission beam and the wave reception beam are respectively focused. The beam width exists inside the cross-section of the pipe, and the pipe axial direction perpendicular thereto. The beam width may be determined in accordance with the material and specification of the ultrasonic wave.

The present invention allows detection of the penetrators of dispersion type having the flaws each with a micro diameter dispersed in the wide region. The welding process may be improved so as not to generate the minute flaw which influences the mechanical characteristics of the welded portion of the welded steel pipe, or the flaw detection may be performed in the manufacturing process so as not to miss any flaw, thus markedly enhancing quality of the welded steel pipe. The pipe may be used under more severe service condition than ever before.

BRIEF DESCRIPTION OF THE DRAWINGS

FIGS. 17A to 17D show the C-scan results at 50 MHz with beam diameter of 100 µm.

FIGS. 18A to 18D show the C-scan results at 50 MHz with beam diameter of 250 µm.

FIGS. 23A and 23B show the comparison between the generally employed method using the non-tandem configulation and the tandem flaw detection method.

FIG. 29 shows the relationship between the focusing coefficient and the beam size.

Figure 1:
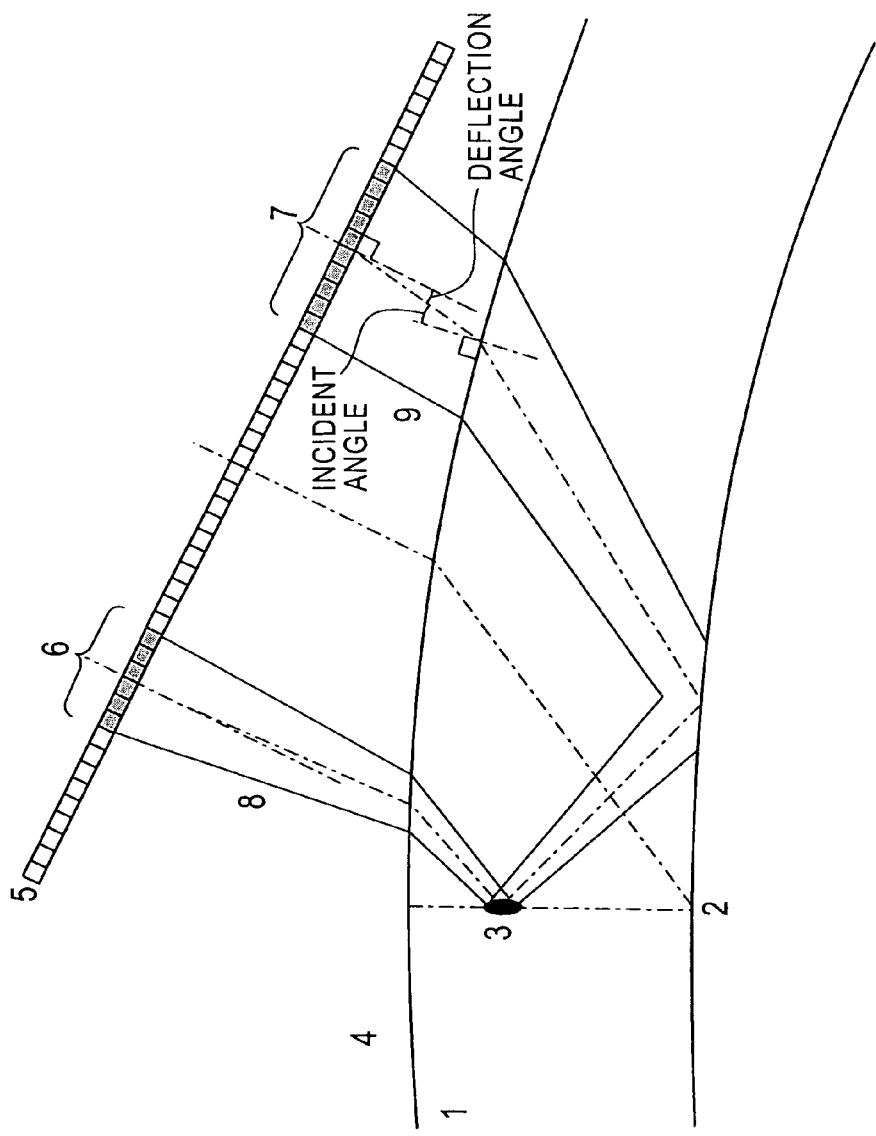
FIG. 1 is an explanatory view of Example 1 according to the present invention.
Figure 2A:
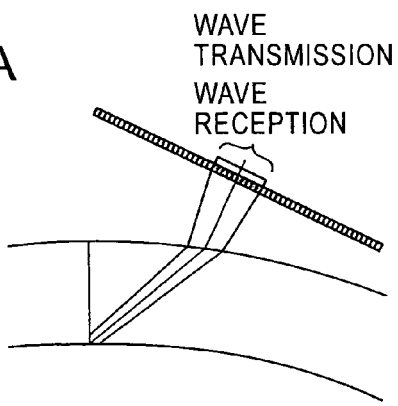
FIGS. 2A to 2D show an exemplary scanning procedure according to Example 1 of the present invention.
Figure 2B:
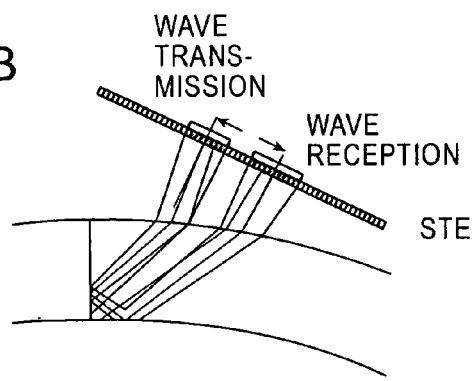
Figure 2C:
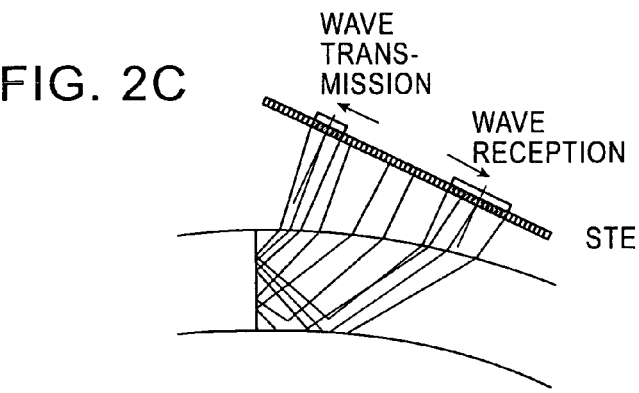
Figure 2D:
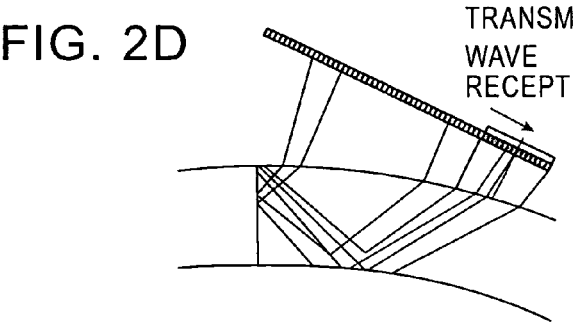

REFERENCE NUMERALS 1 steel pipe
2 welded portion
3 flaw
4 water
5 linear array probe
6 group of transducer elements for wave transmission
7 group of transducer elements for wave reception
8 wave transmission beam
9 wave reception beam
10 flaw detection condition calculation unit
11 delay time set unit
12 pulsar
13 transducer element of linear array probe
14 reception amplifier
15 delay time set unit
16 synthesizing unit
17 gate evaluation unit
30 sample size input unit
31 array probe memory unit
32 aperture control unit
33 gate position memory unit
34 array transmission law memory unit
35 array reception law memory unit
36 array transmission unit

EMBODIMENTS FOR CARRYING OUT THE INVENTION

Various studies have been conducted to discover the new and useful finding that the amount of the minute flaws each having the negligible size (the number of the flaws which exist in a predetermined area) largely influences the mechanical characteristics of the welded portion besides the fact that the minute flaw which resides in the welded portion such as the minute penetrator influences the mechanical characteristics of the welded surface in the pipe axial direction of the electro-seamed welded steel pipe.

The inventors considered that the penetrator size greatly influences the mechanical characteristics of the welded portion of the electric resistance welded pipe, and that the excellent mechanical characteristics owes much to the penetrator with the relatively small size which resides in the welded portion. After searching for the method of detecting those flaws, the inventor conceived the technology for detecting the flaws by reducing the beam width of the ultrasonic waves for wave transmission/reception relative to the generally employed ultrasonic flaw detection method. Then the ultrasonic flaw detection technology having the beam diameter reduced was used to evaluate the existence of the penetrator, and compared the results with the mechanical characteristics. The comparison results, however, were totally different from those expected by the inventors. When the penetrators were detected, good mechanical characteristics were obtained. On the contrary, when the penetrators were not detected, bad mechanical characteristics were obtained. Thereafter, further investigations were conducted to obtain the very useful finding that the penetrator in the form of plural minute flaws each with the size of several μm dispersed in a wide range has the correlation with the mechanical characteristics. Then the ultrasonic flaw detection method for detecting the aforementioned flaws was developed.

Figure 14:
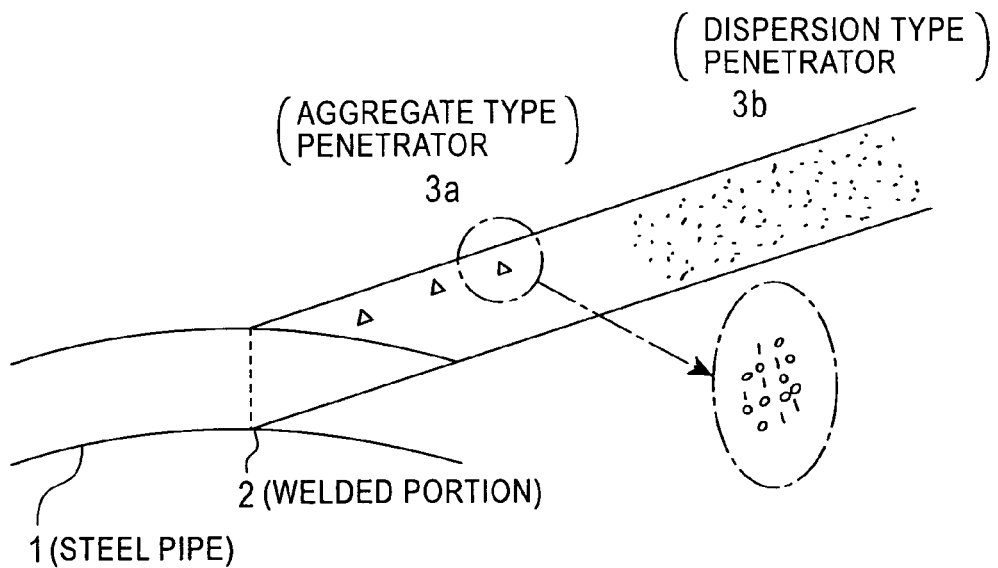
FIG. 14 is a perspective view showing the minute penetrator of the type found from the research of the inventor.

The configuration of the penetrator will be described referring to FIG. 14. Initially the minute flaw such as the penetrator which influences the mechanical characteristics was considered as aggregate of oxides each with several μm (mainly Si—Mn) in the region with several 10 to several 100 μm, which can be seen as the single flaw as indicated by 3a on a welded portion 2 of a steel pipe 1 (in the description, it is referred to as the aggregate type penetrator). The research conducted by the inventors has brought out the penetrator having oxides each with several μm dispersed in the wide region (in the description, it is referred to as the scattered-type penetrator) as indicated by 3b. The scattered-type penetrator cannot be clearly detected by the generally employed detection method. The density of the aforementioned penetrator is too low to observe its cross-section, and accordingly, to clarify the existence. The thorough research conducted by the inventors has demonstrated that it is essential to detect the penetrator of the aforementioned type for evaluating the mechanical characteristics, especially, the level of the excellent characteristics.

[Relationship Between Minute Penetrator Type and Toughness]

Figure 15:
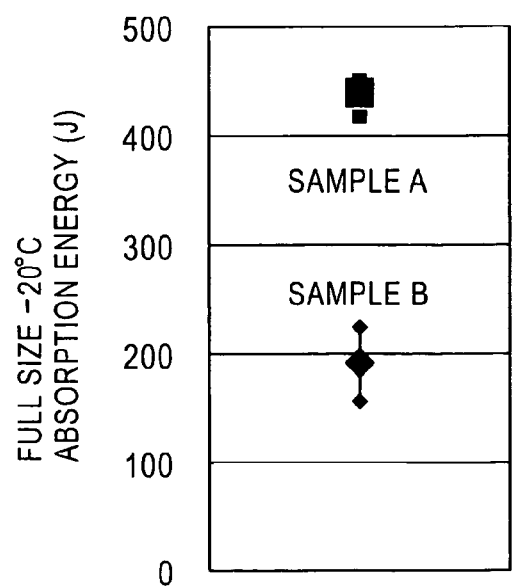
FIG. 15 shows results of the Charpy impact test conducted for the samples.
Figure 16:
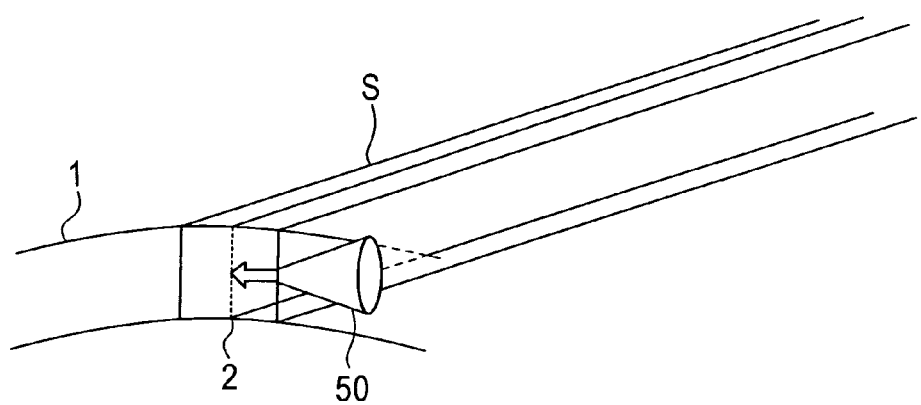
FIG. 16 is a perspective view showing the C-scan method conducted for the seam slice material for the purpose of explaining the principle of the present invention.

FIG. 15 shows the results of Charpy impact test with respect to the Charpy test piece sliced from the sample pipe. The result of the Charpy impact test shows that the sample A (three pieces) was observed to have good mechanical characteristics having absorption energy of 400 J or higher. The sample B (three pieces) was observed to have the absorption energy of approximately 200 J. The welded surface of the welded portion 2 in the pipe axial direction of the electric resistance welded pipe 1 is subjected to the flaw detection through the C-scan method using a focus type ultrasonic probe 50 with respect to the cut surface of the sample S sliced at the position 4 mm apart from the welded surface in the circumferential direction around the area for obtaining the Charpy test piece as shown in FIG. 16. The detection results were compared with the Charpy impact test results. The inventors assumed that aggregate penetrator in the region with several 10 to several 100 μm influences the mechanical characteristics of the welded portion. Then the focus type ultrasonic probe 50 at the frequency of 50 MHz was employed to detect the flaw at the narrowed beam width of 100 μm. The results are shown in FIGS. 17A to 17D. FIG. 17A shows the C-scan data of the sample A, having the x-axis as the pipe axial direction and y-axis as the thickness direction. The signal intensity is indicated with dark/light color (As the signal intensity becomes higher, the color approaches to white). FIG. 17B shows the distribution of the maximum values of the signal intensity with respect to the thickness direction at the same position in the pipe axial direction. The x-axis denotes the pipe axial direction of the pipe, and the y-axis denotes the distribution of the maximum values of the signal intensity. Likewise, FIGS. 17C and 17D show the results of the ultrasonic flaw detection for the sample B. Referring to FIGS. 17B and 17D, the y-axis represents the value of the flaw diameter estimated based on the maximum value of the signal intensity in the thickness direction. The sample A has dispersion of many values each with the signal intensity corresponding to the flaw diameter (corresponding to the aggregate type penetrator as described above) of 50 μm or larger. In case of the sample B, the dispersion of the flaws is hardly observed. The aforementioned results show that the mechanical characteristics become good irrespective of the aggregate type penetrator, and on the contrary, the absorption energy of the sample detected to have substantially no penetrator is low. The results are totally opposite to those estimated by the inventors.

The inventors conducted measurement by changing the measurement conditions. When the beam width was increased (from 100 μm to 250 μm), the signal which had not been recognized was obtained. The results are shown in FIGS. 18A to 18D. In the case of the sample A which provided good mechanical characteristics from Charpy impact test, likewise the case shown in FIG. 17, mostly the signal level corresponding to the flaw diameter of 25 μm far lower than 40 μm was observed. However, the high signal level corresponding to the flaw diameter 100 μm was occasionally observed. Meanwhile in the case of the sample B, no flaw signal corresponding to the high signal level was observed. However, the signal with the intensity corresponding to the flaw diameter of 40 μm (light colored section in the drawing) was observed along the entire axis of the pipe. The inventors found the fact that the widely dispersed flaws each with the diameter approximately 40 μm corresponding to the relatively low signal level greatly influence the mechanical characteristics of the welded portion.

The cross-section of the sample B was observed by the electronic microscope to confirm the sparsely distributed micro oxides (minute penetrator) each with the size ranging from 5 μm to 20 μm in the flaw section on the sample B, which supports the C-scan results.

Figure 19:
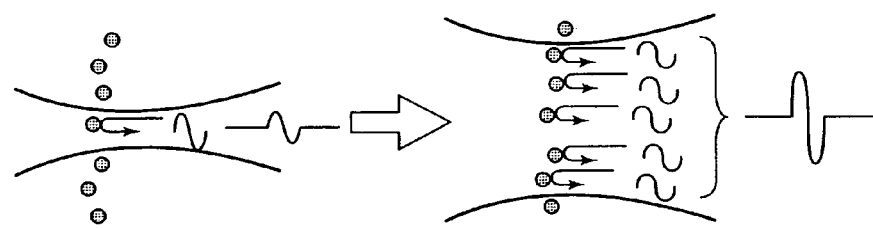
FIG. 19 illustrates the detection of dispersed reflection sources.

The light-colored echo zone detected as a result of increasing the ultrasonic beam width will be discussed. Referring to FIG. 19, in the state where micro reflection sources are uniformly dispersed, the number of the micro reflection sources becomes small in the area with the narrow beam width. The rate of the total flaw area to the beam area is low, thus weakening the reflection echo. Meanwhile, the number of the micro reflection sources becomes large in the area with the wider beam width. The rate of the total flaw area to the beam area is high, and weakened echoes are integrated into the strong one, resulting in the high detection signal level.

In view of the aforementioned results, the penetrator having the flaws each with micro diameter dispersed in the wide region (scattered-type penetrator) influences the mechanical characteristics of the welded portion. Accordingly, such flaw should be detected for the purpose of conducting the accurate evaluation.

Based on the aforementioned findings and analysis, the invention was made with respect to detection of the scattered-type penetrator by subjecting the steel pipe to the ultrasonic flaw detection while being kept intact. The beam focus degree as the general level is insufficient for detecting the scattered-type penetrator. However, the penetrator cannot be detected at the necessarily high beam focus degree. The focus degree for the C-scan method is different from the one for the tandem probe method according to the present invention which allows the detection while keeping the steel pipe intact. It is an essential point of the present invention to discover the beam width range which allows detection of the scattered-type penetrator while conducting the tandem flaw detection for obtaining the required sensitivity.

The array probe is employed in the present invention, and therefore, the beam shape becomes rectangular. The beam width in the present invention may be regarded as the effective value obtained by computing the square root of the beam area. However, there may be the case where the penetrator is continuously formed along the axis of the pipe, and accordingly, no focus in the pipe axial direction is necessary. In such a case, the beam width in the thickness direction of the pipe may be considered.

The inventors researched with respect to the reflection property of the flaw to be detected, and optimum ranges of the incident angle of the ultrasonic wave to the flaw, and the reflection angle of the ultrasonic wave to be received as the reflecting wave from the flaw, which will be described in detail below.

[Analysis on Reflection Property of the Flaw]

As the welded portion is subjected to upsetting to manufacture the welded steel pipe, the minute flaw that exists in the welded portion of the electro-seamed steel pipe such as the penetrator and the cold-junction flaw is likely to be crushed in the circumferential direction. Meanwhile, it may be elongated in directions of the pipe thickness (radial direction) and the pipe axis, that is, the welded plane to have the flat shape.

Figure 20A:
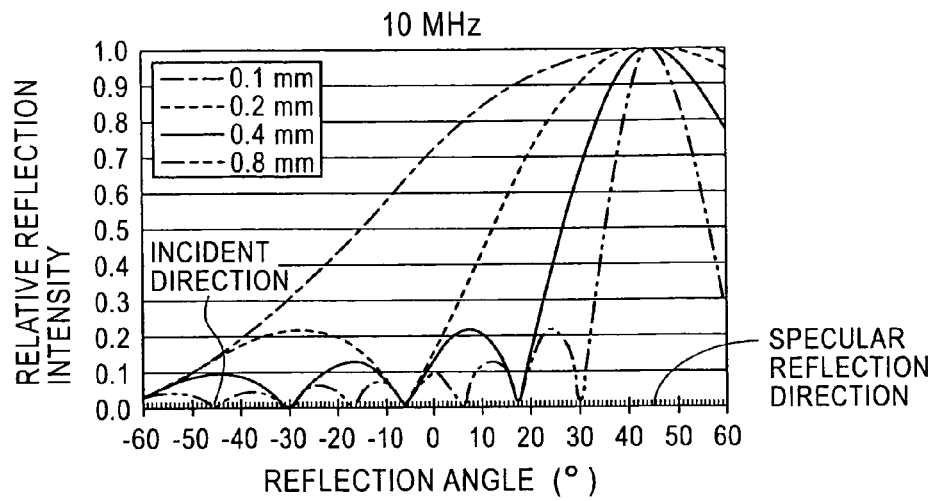
FIGS. 20A to 20C show the relationship between the flaw size and the reflection directivity.
Figure 20B:
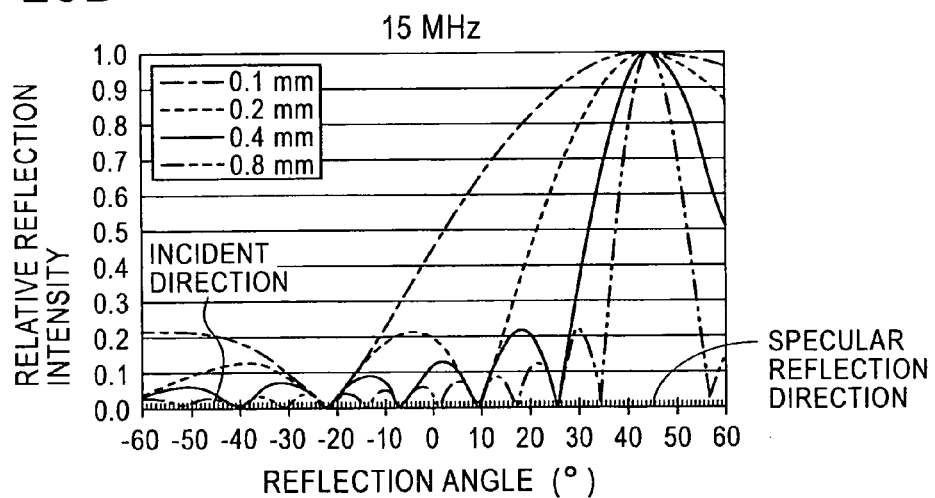
Figure 20C:
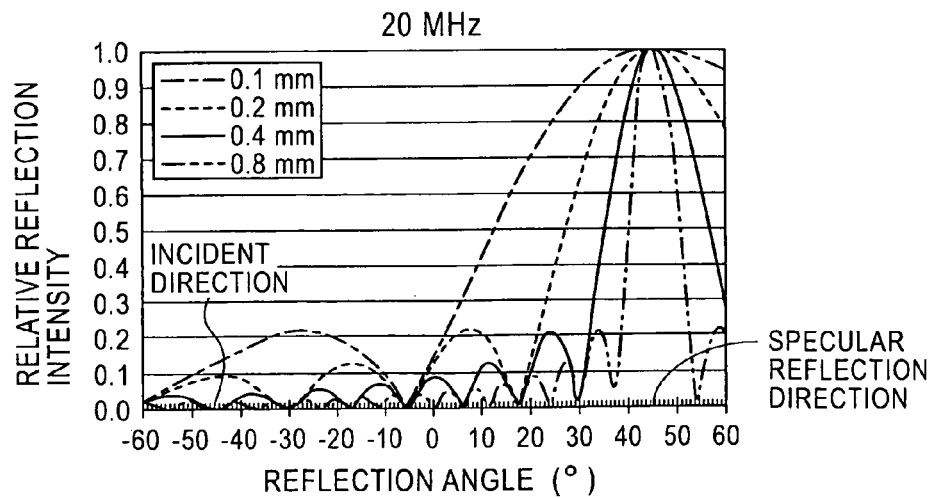
Figure 21:
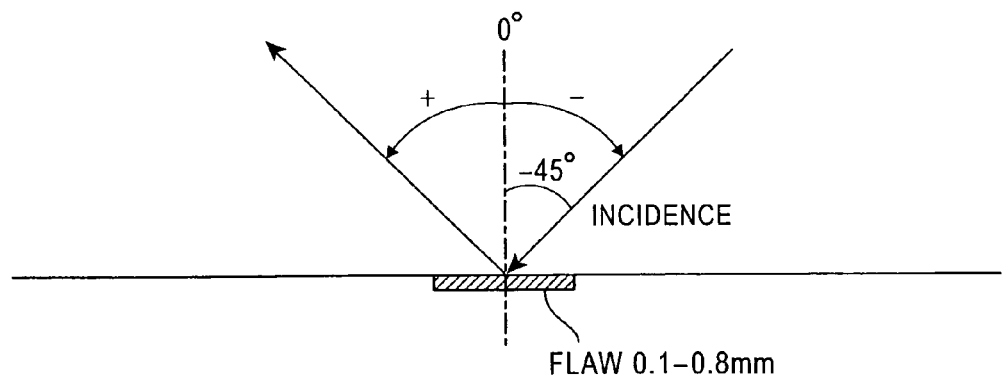
FIG. 21 illustrates the reflection characteristics.

The relationship between the flaw size and the reflection directionality was theoretically evaluated to obtain the results as shown in FIGS. 20A to 20C. The results shown in FIGS. 20A to 20C were derived from the theoretical calculation of the signal intensity at the respective reflection angles in the conditions with incidence of the ultrasonic wave from −45° direction while changing the flaw sizes (equivalent flaw size) to 0.1 mm, 0.2 mm, 0.4 mm, and 0.8 mm corresponding to the respective pipe thickness direction (corresponding to the lateral direction in FIG. 21) at the respective frequencies of 10 MHz, 15 MHz, and 20 MHz. Each y-axis of the respective graphs shown in FIGS. 20A to 20C denotes the standardized relative value with respect to the signal intensity at the mirror reflection angle of 45° as the reference value 1. In either case, the signal intensity of the wave reflecting in the direction of −45° at which the ultrasonic wave is irradiated is considerably low. It is approximately 0.2 or lower of the intensity in the direction at the mirror reflection angle of 45°. In any case, the signal intensity in the mirror reflection direction of 45° becomes the highest.

In case of the flaw with the size of 0.8 mm at 20 MHz having the sharpest directionality in the aforementioned calculation condition, the angle at which the signal intensity becomes half (the value is 0.5 shown in FIGS. 20A to 20C) the one at the mirror reflection angle ranges from 40° to 50°. As the directionality varies depending on the flaw size, the range of the incident angle with respect to the welded portion of the wave reception beam may be determined in accordance with the size of the flaw required to be detected. For example, it is preferable to set the incident angle of the wave reception beam to the welded portion at the value close to 45° for detecting the flaw with larger size without deteriorating the sensitivity. In order to suppress deterioration in the signal intensity of the flaw with the size of 0.8 mm at 15 MHz by half, it is preferable to set the angle to be in the range from 39° to 52°. Conversely, it is preferable to set the angle to be in the range from 33° to 61° for detecting the small flaw with the size equal to or smaller than 0.4 mm at 15 MHz.

The analysis clarifies that the signal intensity of the reflection signal of the ultrasonic wave at the flaw becomes high having the peak at the mirror reflection direction. It is the most preferable to receive the ultrasonic wave in the aforementioned mirror reflection direction. However, the reflection intensity of the signal at the level 50% of that at the peak allows sufficient detection. Accordingly, the detection may be conducted by receiving the ultrasonic wave reflecting in the angular range corresponding to the range as described above.

The result of the reflection directionality of the flaw with the size of 0.4 mm at the frequency of 15 MHz as shown in FIGS. 20A to 20C shows that the reflection angle established when the reflection intensity becomes 50% of that at the peak ranges from 33° to 61°. Accordingly, the preferable range of the angle is from −12° to +16° with respect to the mirror reflection angle of 45° as the reference value. In the case where the flaw with the size up to 0.8 mm at the frequency of 20 MHz is detected, it is preferable to set the range from −5° to +5°. In the aforementioned examples, the reflection angle characteristics are indicated based on the incidence to the flaw at 45°. The incident angle characteristics obtained when the opposite reflection angle is set to 45° may be the same as those described above. If the incident angle is other than 45°, substantially the same characteristics may be obtained so long as the angle is in the incident angle range which clears the condition for the mode conversion loss to be described later.

Based on the reflection characteristics of the flaw, the structure of the ultrasonic sensor is evaluated as described below.

[Tandem Configuration]

Based on the findings with respect to the flaw reflection characteristics, it is preferable to form the ultrasonic probe for wave reception at the position different from that of the ultrasonic probe for wave transmission, that is, the tandem configulation for the purpose of receiving the ultrasonic wave reflecting in the predetermined angle range having the mirror direction at the flaw as the center. However, plural probes have to be provided so as to conduct the thorough inspection in the thickness direction (radial direction) of the welded portion using the point focus type probe as disclosed in Patent Document 1. The diameter of the opening is required to be large for focusing the beam to detect the flaw with smaller size. However, it is very difficult to realize the aforementioned requirements into the actual structure from the aspect of both engineering and cost.

In the present invention, the tandem configuration is employed using the array probe provided with different transmission unit and reception unit. The use of the array probe allows the focus point of the ultrasonic beam to be scanned from the inner surface side to the outer surface side (or outer surface side to the inner surface side, which may be arbitrarily determined) in the thickness direction of the welded portion by switching the group of transducer elements between the transmission unit and the reception unit, and/or the refraction angle between the wave transmission and the wave reception sequentially. This makes it possible to detect the flaw from the inner surface side to the outer surface side without forming the dead zone. The use of the array probe easily changes the scan range and the focus position in spite of the change in the pipe size, thus simplifying the preliminary adjustment. The transducer elements of the array probe are selected to be formed into the tandem configuration such that the inspection is thoroughly conducted in the thickness direction.

The tandem configuration has the advantage of improving the sensitivity by receiving the reflection wave in the predetermined angular range with respect to the mirror reflection direction. Besides, the effect for improving the other type of sensitivity may be provided. It is clarified that the tandem configuration is essential to ensure detection of the minute flaws.

Figure 22A:
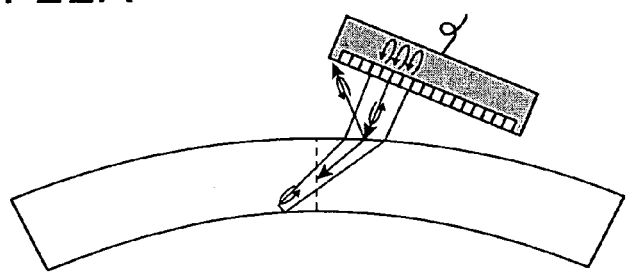
FIGS. 22A and 22B graphically show the comparison between the non-tandem configulation and the tandem configulation.
Figure 22B:
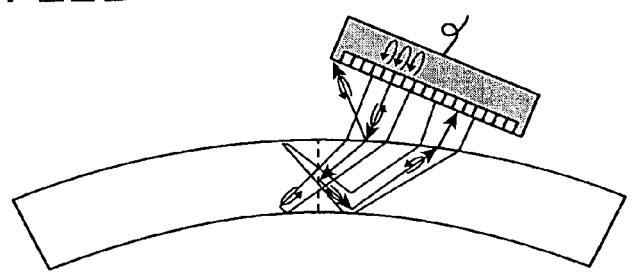

FIGS. 22A and 22B show the non-tandem configuration and the tandem configuration, respectively for the comparative purpose. FIG. 22A shows the use of the array probe for subjecting the welded portion to the flaw detection through the general reflection method having the wave transmission unit and the wave reception unit formed as the single structure. The ultrasonic wave is irradiated from the group of transducer elements of the array probe into the pipe while refracting on the outer surface of the pipe to reach the welded portion. The ultrasonic wave may reflect at the flaw, if any, to enter into the group of transducer elements which has transmitted the wave while following the same path as the wave transmission so as to be received. Upon reception, the echo inside the array probe, the diffusely reflecting wave caused by the outer surface roughness of the pipe, reflection wave reflecting at the outer surface of the pipe at the array probe and the holding portion thereof, and the reflection wave caused by the inner surface roughness of the pipe and the cut bead residual may be directed to the array probe besides the reflection wave from the flaw. In the generally employed reflection method, the aforementioned unnecessary reflection waves, that is, noise may be received while being superimposed with the flaw signal. Accordingly, the detection is conducted with deteriorated signal intensity and the S/N ratio. It is further difficult to eliminate such noise.

FIG. 22B shows the tandem flaw detection using the tandem configuration with different groups of transducer elements for the wave transmission and the wave reception, respectively according to the present invention. The ultrasonic wave is irradiated from the group of transducer elements for the wave transmission of the array probe, and refracts at the outer surface of the pipe thereinto to reach the welded portion. The ultrasonic wave reflects at the flaw, if any, and advances with the highest intensity toward the mirror reflection direction. It reflects at the inner surface of the pipe later to reach the outer surface of the pipe. It then refracts to enter into the group of transducer elements for the wave reception so as to be received. As the ultrasonic wave follows the aforementioned path, the echo inside the array probe, diffused reflection caused by the outer surface roughness of the pipe, reflection at the outer surface to further reflect at the array probe and the holding portion thereof, the reflection caused by the inner surface roughness of the pipe and the cut bead residue may be directed to the group of transducer elements for the wave transmission entirely, but not directed to reach the group of transducer elements of the wave reception. That is, the signal received by the group of transducer elements for wave reception in the tandem configuration is not superimposed with the noise echo owing to the diffused reflection of the ultrasonic wave under no influence of the noise to obtain considerably high S/N compared with the general reflection method as shown in FIG. 22A. The effects resulting from the reflection wave in the mirror reflection direction and the noise suppression may be obtained, ensuring to detect the minute flaw.

FIGS. 23A and 23B show flaw detection results of the generally employed method for the wave transmission/reception performed by the same probe in the non-tandem configulation, and the tandem flaw detection according to the present invention.

FIG. 23A shows the flaw detection image data derived from the generally employed method. FIG. 23B shows the flaw detection image data derived from the present invention. Referring to FIGS. 23A and 23B, the higher the signal intensity becomes, the lighter the color of the image becomes.

As the aforementioned results show, the noise is caused by the inner surface roughness in the general reflection method. The reflection from the inside of the wall of the pipe is interrupted by the noise to be weakened, and is hardly detected. Meanwhile, in the present invention; the noise caused by the inner surface roughness is weakened, and accordingly, the reflection including the one from the inside of the wall may be clearly detected.

It is discovered that the tandem configuration improves the detection performance compared with the related art, and at the same time, some difficulties upon application of the present invention to the pipe with curvature. The effort for eliminating the difficulties will be described hereinafter.
[Examination with Respect to Mode Conversion Loss]

It is discovered that the tandem configuration is capable of sufficiently improving the sensitivity. However, the attenuation of the signal intensity caused by the "mode conversion loss" has to be prevented upon reflection at the inner/outer surfaces of the pipe and the flaw in the course of propagation of the ultrasonic wave inside the pipe for the purpose of allowing the tandem configuration to maintain the improved sensitivity. The mode conversion loss lowers the detection sensitivity owing to the attenuation of the signal intensity as a result of conversion from the lateral ultrasonic wave irradiated to the steel pipe into the longitudinal ultrasonic wave under the reflection condition. The aforementioned phenomenon will be described referring to the drawing.

Figure 24A:
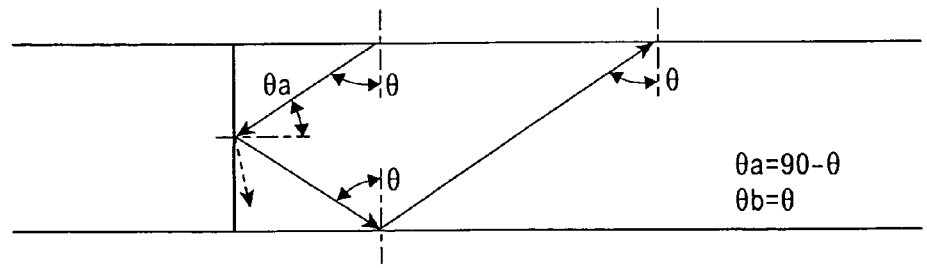
FIGS. 24A and 24B graphically show the mode conversion loss on the flat steel plate.
Figure 24B:
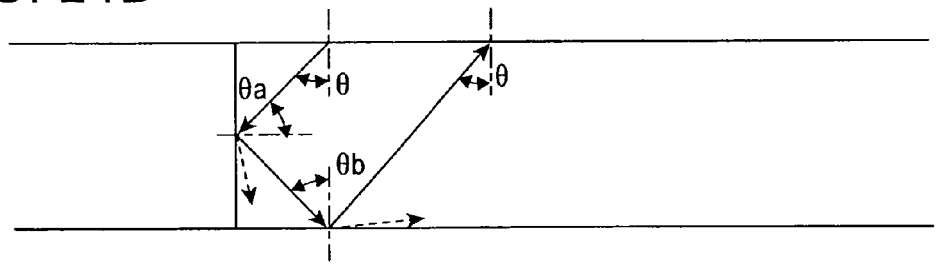

FIGS. 24A and 24B show the mode conversion loss in the flat steel plate. FIG. 24A shows the flaw detection in the tandem configuration of the flat steel plate (hereinafter referred to as a tandem flaw detection). In the case where the refraction angle of the lateral ultrasonic wave irradiated to the flat steel plate is set to $\theta$, an incident angle $\theta a$ to the welded surface becomes $(90°-\theta)$, and an incident angle $\theta b$ to the bottom surface becomes $\theta$. In the steel, when the lateral ultrasonic wave is irradiated at the incident angle of approximately 33° or smaller upon reflection of the lateral ultrasonic wave at the welded portion and the steel plate bottom surface, the longitudinal ultrasonic wave is generated in the direction indicated by the dotted line via the mode conversion at the reflection.

Figure 24C:
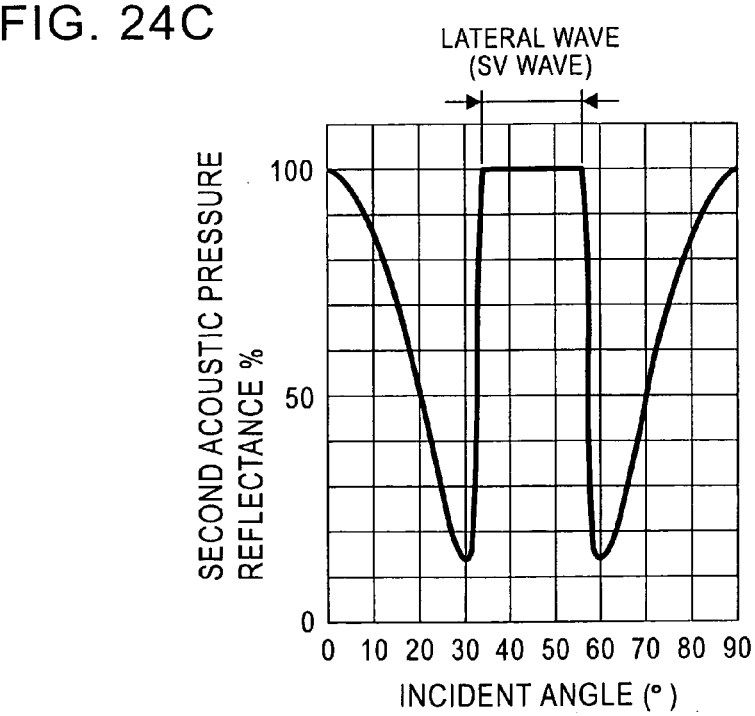
FIG. 24C is a graph depicting the change in the reflectance with respect to incident angle.

Referring to FIG. 24A, if the angle $\theta$ is large (approximately 57° or larger), the incident angle $\theta a$ is reduced (approximately 33° or smaller), and accordingly, mode conversion occurs by the reflection at the welded portion. Referring to FIG. 24B, if the angle $\theta$ is small (approximately 33° or smaller), no mode conversion occurs by the reflection at the welded portion. However, as the incident angle $\theta b$ becomes approximately equal to or smaller than 33°, the mode conversion occurs. Upon mode conversion from the shear wave into the longitudinal wave, the intensity of the ultrasonic wave in the tandem flaw detection direction is weakened, resulting in deteriorated detection sensitivity. The phenomenon that the mode conversion from the shear wave to the longitudinal wave of the ultrasonic wave occurs upon reflection to attenuate the intensity of the lateral ultrasonic wave will be referred to as the mode conversion loss. FIG. 24C shows the change in the reflection intensity when the ultrasonic wave reflects twice on the welded portion surface and the inner surface with respect to the incident angle. As indicated by the drawing, the mode conversion loss never occurs by setting the incident angle ranging from 33.2° to 56.8° as the theoretical value.

In case of the flat steel plate, the relative angle defined by the array probe surface and the upper surface of the flat steel plate is kept constant irrespective of the position. Examination on the relative angle of the array probe surface with respect to the upper surface of the flat steel plate, and the angle of the wave transmission beam with respect to the probe surface at an arbitrary position allows easy determination with respect to the refraction condition whether or not the mode conversion loss occurs even if the group of transducer elements which constitute the wave transmission unit and the wave reception unit are moved for scanning the welded surface with the ultrasonic beam.

Figure 25A:
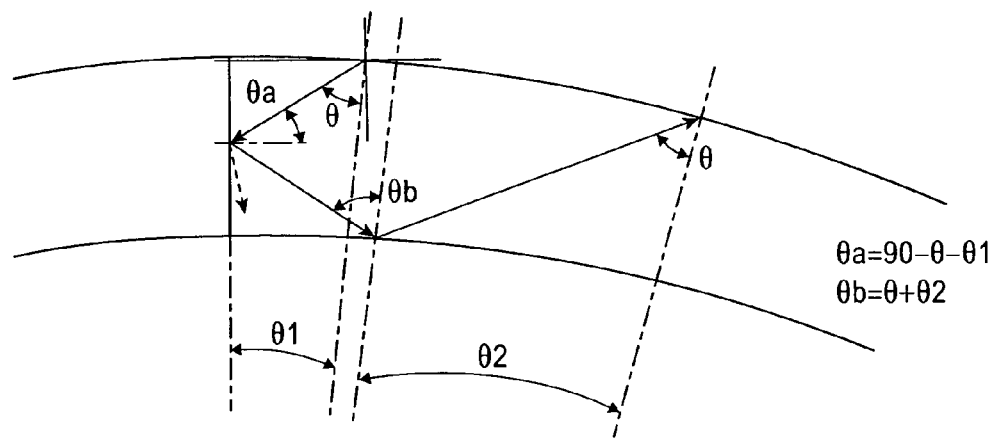
FIGS. 25A and 25B graphically show the mode conversion loss on the steel pipe.
Figure 25B:
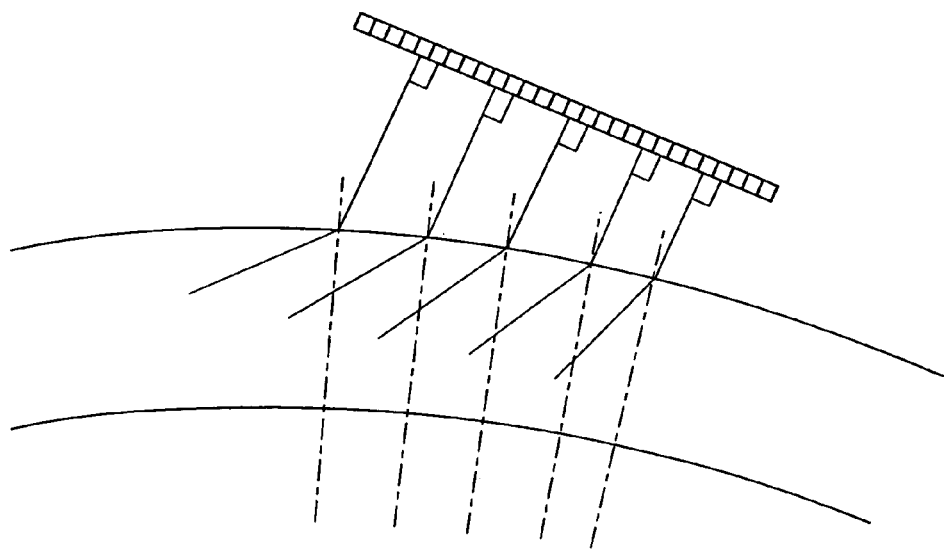

However, it is difficult to conduct the tandem flaw detection on the steel pipe compared with that on the flat steel plate because of the curvature, which will be described referring to FIGS. 25A and 25B. Likewise the flat steel plate, it is assumed that the ultrasonic wave is irradiated to the steel pipe from the array probe at the refraction angle of $\theta$ relative to the reference angle with respect to the welded surface set to 0°. The incident point (incident position) to the outer surface of the steel pipe is set such that the angle defined by the normal direction of the outer surface at the incident point and the welded surface becomes $\theta 1$. The incident angle $\theta a$ at this time does not become $(90°-\theta)$, but $(90°-\theta 1\ \theta 1)$. The incident angle $\theta b$ to the bottom surface does not become $\theta$, but $(\theta+\theta 2)$.

In the aforementioned case, the relationship of $\theta 1<\theta 2$ is established, and accordingly, the refraction angle range where the mode conversion loss does not occur may be narrowed by $\theta 2$ at maximum compared with the case for inspecting the flat steel plate. Assuming that the steel pipe with thickness t/outer diameter D of 3.4% has the refraction angle of approximately 45°, the angle $\theta 2$ is approximately 4°. The corresponding refraction angle range where the mode conversion loss does not occur is narrowed from 37° to 53°. In view of the realistic size of the steel pipe, the angle $\theta 2$ may be in the range from 1.7° to 11.25°.

Most size of the steel pipe may be covered from the minimum value to 5% of t/D. In case of t/D as 5%, the angle $\theta 2$ becomes 6.8°. In this case, the corresponding refraction angle range ranges from 40° to 50°.

In consideration with the steel pipe with the curvature relative to the general array transducer element with straight form, upon the wave transmission of the ultrasonic beam at the constant angle (90° to the probe surface as shown in the drawing) likewise the flat steel plate, the incident angle to the steel pipe does not become constant, and accordingly, the refraction angle does not become constant. Assuming that the steel pipe has the width of the beam scan from the array transducer element is twice the wall thickness, and the t/D of 3.4%, the refraction angle varies in the range from 31° to 62° within the scan width even if the probe is disposed so as to set the refraction angle of 45° at the center. The angle exceeds the range where the mode conversion loss does not occur.

The beam is required to be controlled such that the refraction angle is kept in the set range to prevent the mode conversion loss on the welded surface and the bottom surface in consideration with the curvature of the steel pipe for solving the aforementioned problem. Otherwise, the tandem flaw detection with respect to the steel pipe cannot be performed with the high sensitivity. The incident angle to the welded surface and the inner surface of the pipe is converted into the refraction angle in the range from 35° to 55° in consideration with the angle $\theta 2$ with respect to the theoretical value of the incident angle at the minimum value of the t/D.

As the scanning with the ultrasonic beam is conducted while moving the measurement point, the incident angle (refraction angle) of the ultrasonic wave to the steel pipe changes. The determination whether or not the angle becomes the value which causes the mode conversion loss cannot be easily made, or there is no specific method for the aforementioned determination.

The inventors realize to set the incident angle not to cause the mode conversion loss through the method for determining the scanning line to be described hereinafter.

The procedure for setting the refraction angle to be in the range which does not cause the mode conversion loss will be described.

1) The refraction angle is determined to set the position and angle of the array probe 1)-1: In consideration with the incident angle $\theta a$ to the welded surface, the refraction angle $\theta$ is determined. The theoretical incident angle to the welded surface not to cause the mode conversion loss establishes the relationship of $33.2°\leq a\leq 56.8°$. The incident angle to the welded surface does not have to be kept constant and may be changed so long as the angle is within the above range upon scanning on the inner/outer surface of the welded surface in the width direction of the pipe. The case for keeping the refraction angle $\theta$ constant will be described for the purpose of simplifying the calculation. In this case, the incident angle $\theta a$ to the welded surface is calculated by the equation of $\theta a=90°-\theta-1$, and the angle $\theta 1$ changes depending on the position in the thickness direction of the welded portion in the range from 0 to $\theta 2$ (for example, $\theta 1=\theta 2$, and $\theta 1=0$ on the inner and the outer surface sides, respectively). Under the condition where $\theta 2=4°$ at the refraction angle of 45°, the angle $\theta a$ ranges from 41° to 45°. Under the condition where the refraction angle is set to 47° upon incidence to the point of the welded portion around the center of the wall thickness, the angle $\theta a$ at the center of the welded portion in the wall thickness direction becomes substantially 45°. The angle $\theta a$ will be in the range from 43° to 47° when scanning on the inner/outer surfaces.

1)-2: The position and the angle of the array probe are determined such that the beam is vertically transmitted from the transducer element at the center of the array probe to the probe surface at the predetermined refraction angle (for example, 45°), and the lateral ultrasonic wave is irradiated from the outer surface of the pipe to the position of the welded surface at the end of the inner surface (or the end of the outer surface) at the predetermined incident angle (for example, 41° in the aforementioned example).

2) The position at which the scanning line transmitted/received from the respective transducer elements of the array probe is irradiated to the outer surface of the pipe is determined.

2)-1: As one of various methods for making the determination, the outer surface of the pipe is scanned with respect to the subject transducer element (or the position between the transducer elements) to calculate the refraction angle $\theta$ defined by the transducer element position, the outer surface scanning position and the outer surface tangent line. Then the incident position on the outer surface as the value set in the section 1)-1 is determined. Specifically, the scanning line obtained by connecting the transducer elements to the respective points on the outer surfaces (for example, the points locate at uniform intervals or arbitrary interval on the outer circumference) with straight lines. Each of the refraction angles θ for the respective scanning lines is calculated to select the scanning line at the angle θ which is the same as or the closest to the predetermined angle. Then the incident position of the scanning line is determined.

2)-2: The propagation path after incidence to the pipe is geometrically obtained based on the transducer element position, the incident position on the outer surface set by the section 2)-1, and the pipe configuration (diameter and thickness) to calculate the incident position to the welded surface.

3) The positioning is performed at the center of the array probe, and the aforementioned process is performed while keeping the refraction angle constant. This makes it possible to provide a combination (pair) of the route of the propagation path (scanning line) calculated in the section 2)-2 on the welded surface symmetrically with respect to the scanning line at the center of the array probe. The pair is referred to as the scanning line of the wave transmission/wave reception, each serving as the center transducer element for the wave transmission/reception units (the group of transducer elements for the wave transmission/reception units are formed having the transducer elements at the center). If the number of the transducer elements is even, the center position is corrected to the boundary between the adjacent transducer elements so as to perform the aforementioned process. The calculation is performed while keeping the refraction angle θ constant. However, the calculation may be performed while keeping the incident angle θa to the welded surface kept constant. Alternatively, both angles θ and θa may be changed.

The use of the array probe capable of appropriately controlling the group of transducer elements or with the curvature may bring the incident angle and the refraction angle into the theoretical range where the mode conversion loss does not occur. The refraction angle suitable for the flaw detection by the shear wave may be in the range from approximately 30° to 70°. In consideration with the angle dependence of the sound pressure reflectance upon reflection of the shear wave at the flaw and the inner surface, it is preferable to set the refraction angle to be in the range from approximately 35° to 55° corresponding to the total reflection. It may be in the range from 40° to 50° in consideration with the stability. It is the most preferable to set the refraction angle of the wave transmission to be the same as that of the wave reception. However, as the reflection directionality of the flaw is broad, those refraction angles may be different within the range of the reflection directionality.

[Control of Constant Incident Angle]

Figure 26:
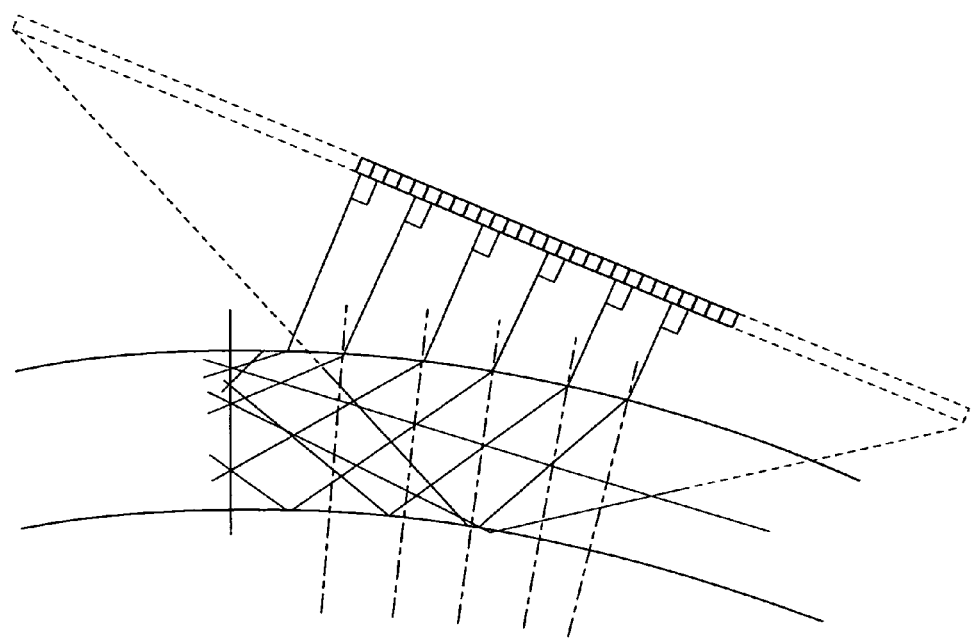
FIG. 26 shows an exemplary propagation path.

The generally employed array probe with the straight shape is disposed along the circumferential surface of the pipe with the curvature for applying the array probe with the tandem configuration. When the group of transducer elements for the wave transmission/reception units displace on the array, the incident angle to the pipe may differ between one wave transmission/reception and the other. The aforementioned phenomenon is shown in FIG. 26 which represents the example of the propagation path on the pipe. The beam shown by the solid line represents the established relationship between the wave transmission and the wave reception. The other beam shown by the dashed line represents that the relationship between the wave transmission and the wave reception cannot be established due to different incident angle.

There may be the case where the wave transmission unit may be disposed in the array probe, but the wave reception unit is located outside the array probe (as shown by the dashed line). In the aforementioned case, the group of transducer elements for the wave transmission and the wave reception units cannot be arranged to have the tandem configuration in the range of the array probe. The inventors tried to keep any one of the incident angle or preferably, both incident angles at the wave transmission side and the wave reception side to be kept constant through the scanning to keep the refraction angle inside the pipe such as the steel pipe constant. The problem as described above, thus, hardly occurs.

Figures 4A, 4B:
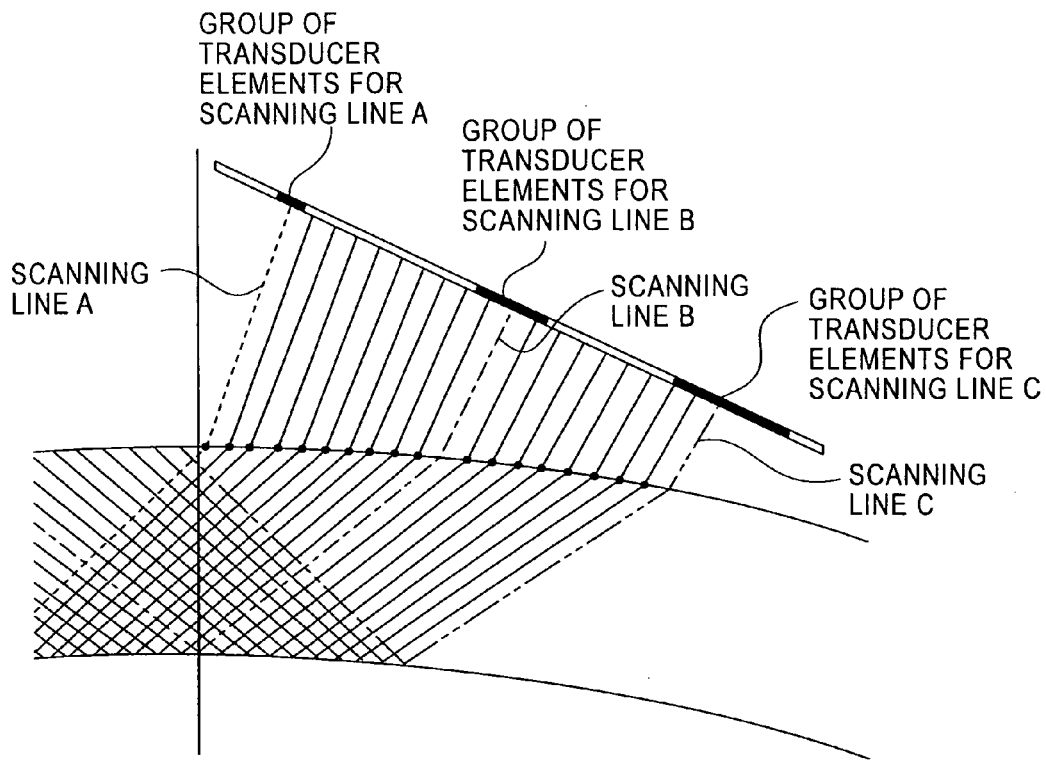
FIGS. 4A and 4B show an example of the scanning line and calculation results of the flaw detection condition with respect to representative points.

Referring to FIGS. 4A and 4B showing the use of the similar array probe to the one shown in FIG. 26, as the refraction angle is kept constant, all the combinations of the wave transmission units and the wave reception units may be disposed within the array probe. For example, if each of the outer surface side and the inner surface side of the steel pipe is formed as a true circle at the constant refraction angle, the positional relationship between the wave transmission and the wave reception may be geometrically obtained easily. Even in the case where the inner surface side is not formed as the true circle owing to the change in the wall thickness of the steel pipe, the path where the reflection of the incidence to the welded surface may be easily obtained as the outer surface side of the steel pipe has the true circle shape. The subsequent path may be theoretically or experimentally determined in consideration with the shape of the inner surface side.

The incident angle may be kept constant by controlling the respective transducer elements of the group of transducer elements for the wave transmission unit and the wave reception units from the array probe. The group of transducer elements may be selected through the aforementioned method. The other control method will be described later.

Alternatively, the incident angle may be kept constant by forming the array probe itself into the configuration with the curvature which is substantially the same as that of the pipe for controlling the transducer elements.

[Optimum Beam Width Range]

Figure 27A:
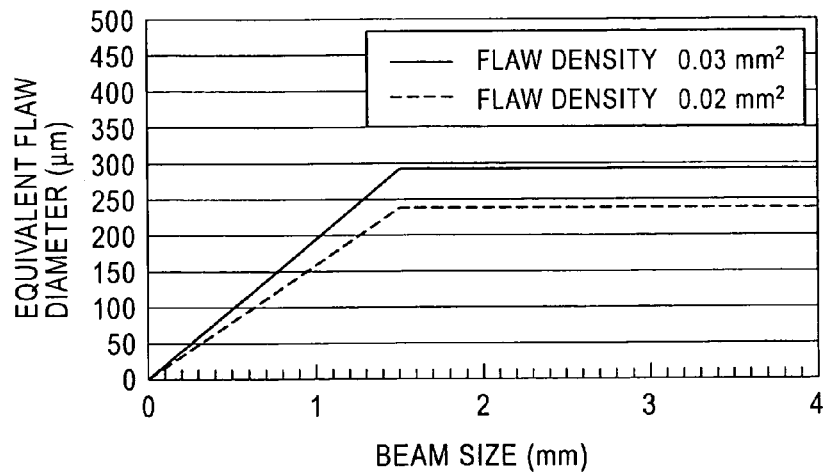
FIGS. 27A to 27C show the relationship between the beam size and the signal intensity.
Figure 27B:
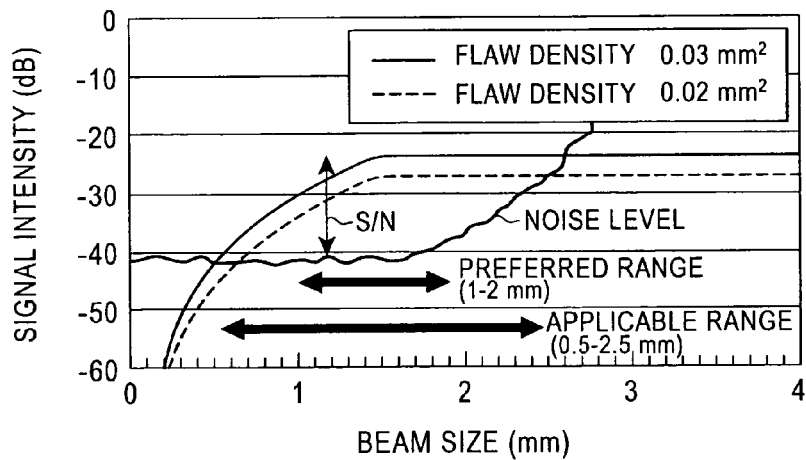
Figure 27C:
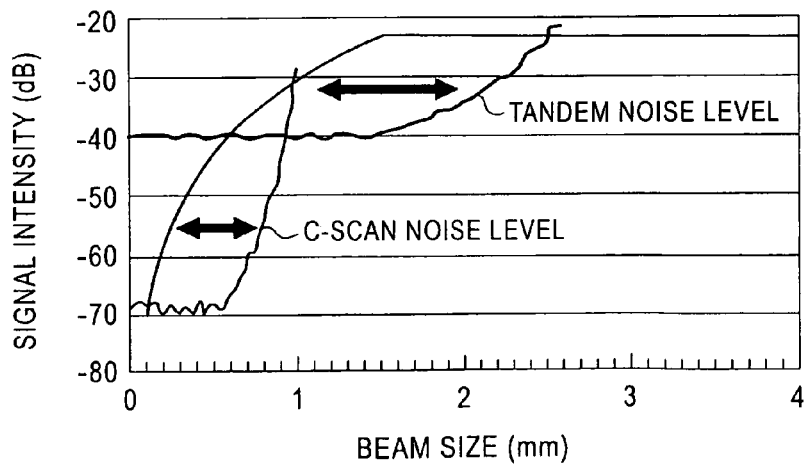

FIG. 27A shows a relationship between the beam width (beam width corresponding to one side of the square, which is referred to as the beam size in FIGS. 27A to 27C) and the equivalent flaw diameter (the flaw diameter corresponding to the total flaw area in the beam). The graph shows the equivalent flaw diameter as the total flaw area inside the ultrasonic beam, which is theoretically calculated when changing the beam width (beam size) in two kinds of the flaw density of 0.03 mm$^2$ and 0.02 mm$^2$, respectively. As the beam width increases, the equivalent flaw diameter becomes large up to the beam width of 1.5 mm or larger. Subsequently, the value is kept constant. The aforementioned value is saturated as it is assumed that the distribution range of the scattered-type penetrator has the size of 1.5 mm×1.5 mm in the analysis.

FIG. 27B shows the signal intensity expressed in dB, which is calculated from the sound pressure reflectance corresponding to the equivalent flaw diameter shown in FIG. 27A upon the tandem flaw detection. The noise level of −40 dB schematically shows the level actually obtained upon the tandem flaw detection. The noise level is raised at the side of the large beam width (beam size) because the noise level is raised by detecting the noise caused by the inner/outer surface roughness as the beam width is increased. The graph shows that the beam width ranging from 0.5 to 2.5 mm is applicable as the range where the noise level is lower than the signal level in the tandem flaw detection. In the case of the flaw density of 0.02 mm$^2$, the signal intensity is slightly lowered. Accordingly, the range from the beam width from 0.7 mm to 2.5 mm is applicable. It is required to have the difference between the signal level and the noise level by 5 dB or higher for improving the S/N ratio. Accordingly, the range from 1 to 2 mm is preferable.

FIG. 27C shows the signal intensity of the equivalent flaw diameter expressed in dB for the purpose of comparing between the tandem flaw detection and the C-scan. FIG. 27C shows the signal level only in the case of the flaw density of 0.03 mm². The noise level of the C-scan is lower than the tandem flaw detection because of good conditions as the single probe, closer water equivalent traveling distance, and polished surface. Meanwhile, if the beam width (beam size) exceeds 1 mm, the S/N ratio is deteriorated under the influence of the sample side surface (beam propagation path is interrupted, and diffused reflection occurs on the side surface of sample to pick up the resultant noise signal)(strictly, the effective flaw detection region becomes too narrow to be available for the evaluation). Referring to the drawing, the range applicable to the beam size for the C-scan is from 0.2 to 1 mm. The focus degree in the tandem flaw detection according to the present invention is different from the one in the C-scan for the purpose of improving the sensitivity.

It is an object to conduct the inspection for the quality assurance and the quality control while keeping the steel pipe intact in the manufacturing step. Therefore, calculation of the optimum value of the beam width (beam size) in the C-scan method has little significance. Calculation of the optimum value of the beam width (beam size) in the tandem flaw detection which allows the on-line or in-line inspection has the significance. Accordingly, the applicable range of the beam width is obtained.

Figure 28:
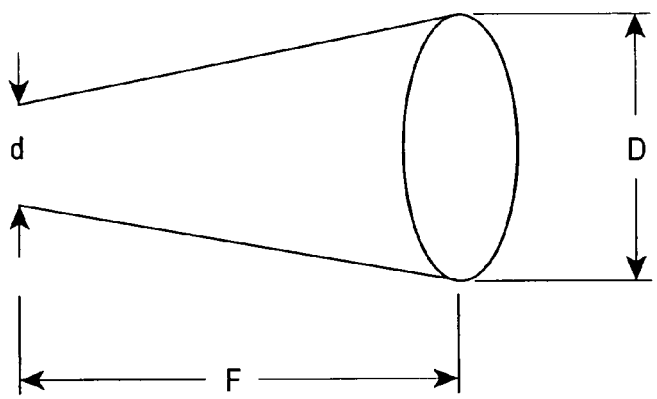
FIG. 28 shows the relationship between the aperture and the beam size.

In the tandem flaw detection, an aperture D of the transducer element for obtaining the beam width d is calculated by the following formula.

$$D = \lambda \cdot \frac{F}{d \cdot \sin\theta} \cdot \frac{\cos\theta w}{\cos\theta} \quad (1)$$

where the code d denotes the beam width at the flaw detection position, F denotes the focus distance, λ denotes the wavelength, θ denotes the refraction angle, and θw denotes the incident angle as shown in FIG. 28.

Supposing that the water equivalent traveling distance is set to 30 mm, the path length within the steel is set to 24 mm, the refraction angle θ is equal to 45°, and the incident angle θw is equal to 18.9°, the focus distance F may be calculated by the equation of 30+24/1480×3230=82 mm. Supposing that the frequency is set to 10 MHz, the wavelength λ may be calculated by the equation of 1480/10 MHz=0.148 mm. The aperture D for obtaining the beam width d=1.5 mm may be obtained as 15 mm from the formula (1).

The number of the transducer elements of the group of transducer elements may be obtained by the thus calculated aperture. The number of the transducer elements of the group of transducer elements for each scanning line may be kept constant. However, the number of the transducer elements may be changed for each of the scanning lines for the purpose of making the sensitivity further uniform. In the case of the tandem flaw detection using the array probe, the transducer element closer to the welded portion among the group of transducer elements has the short focus distance, and the transducer element remotely from the welded portion has the long focus distance. Then the aperture is obtained such that the beam width is within the aforementioned range or the beam width is kept constant in consideration with the focus distance F in accordance with the transducer element position to determine the number of the transducer elements to be excited simultaneously. The control for conducting the simultaneous excitation of the number of the transducer elements corresponding to the aperture may be conducted. The number of the transducer elements to be simultaneously excited denotes the number of those in the group of transducer elements for the single wave transmission and wave reception. The delay time for each element of the group of transducer elements may be set for controlling the focus and the deflection.

When the beam width is kept constant by changing the number of the transducer elements, each number of the transducer elements of the group of transducer elements for the wave transmission/reception is decreased as they are getting closer to the welded portion, and is increased as they are getting remotely from the welded portion. As described above, the beam width d is set to be in the optimum range to allow the flow detection of the scattered-type penetrator having the minute flaws distributed in the wide range with the uniform detection sensitivity from the inner surface side to the outer surface side.

[Condition for Focusing Ultrasonic Beam]

The beam width of the ultrasonic wave to be transmitted and received has to be in the range from 0.5 to 2.5 mm for evaluating the mechanical characteristics of the welded portion of the electro-seamed welded steel pipe in the tandem flaw detection. Meanwhile, the optimum range of the focusing coefficient as one of the parameters for defining the beam focus degree will be discussed. The focusing coefficient J denotes the increase in the sound pressure at the focus position.

$$J = 20\log\left(\frac{D^2}{4\lambda F}\right) \quad (2)$$

where the code D denotes the aperture width of the transducer element, F denotes the focus distance, and λ denotes the wavelength. In the formula (2), the values corresponding to those obtained by the underwater conversion may be used for the focus distance F and the wave length λ.

FIG. 29 shows theoretical calculation results with respect to the relationship between the focusing coefficient and the beam width (beam size referred in FIG. 29) using the formula (2) under the condition where the frequency is set to be in the range from 5 MHz to 15 MHz, and the focus distance F is set to be in the range from 60 mm to 80 mm (substantially equal to the range of the wall thickness of the steel pipe from 10 mm to 16 mm). As the drawing shows, when the beam width (beam size) is small, the focusing coefficient is increased, and when the beam width is large, the focusing coefficient is decreased. As the focusing coefficient indicates the acoustic pressure increase, it is preferable to make the value as large as possible. However, upon detection of the scattered-type penetrator where the minute flaws are dispersed in the wide range, if the focusing coefficient is made large, the beam width becomes too small to be within the optimum range. It is essential to consider the beam width to be in the optimum range. For example, the focusing coefficient in the range from −13 dB to 28 dB is applied for the beam width of the ultrasonic wave ranging from 0.5 to 2.5 mm applicable for detecting the scattered-type penetrator. However, the focusing coefficient in the range of −5 to 20 dB may be applied in consideration with the balance with the beam width. The focusing coefficient ranging from −10 to 5 dB is applicable with respect to the beam width in the appropriate range from 1.0 to 2.0 mm.

[Counter Measure Against Seam Displacement]

It is difficult to keep the positional relationship of the array probe by following the seam because of the slight seam displacement which may prevent the scanning line of the wave transmission from intersecting the scanning line of the wave reception on the welded line.

Under the condition where the focus position of the wave transmission beam coincides with that of the wave reception beam at the welded portion of the pipe disposed on the normal design position, the group of transducer elements for the wave transmission/reception are arranged, and/or the refraction angles upon wave transmission/reception are set such that the focus position of at least the wave transmission beam and the wave reception beam is located at the plural different positions in the longitudinal direction (radial direction of the pipe) and the lateral direction (circumferential direction of the pipe). Any combinations of the scanning lines intersect on the welded line in spite of displacement of the seam position, thus enabling detection of the reflecting wave from the flaw.

EXAMPLE 1

An example of the present invention will be described referring to the drawings. FIG. 1 shows Example 1 according to the present invention. Referring to the drawing, a reference numeral 1 denotes a steel pipe as an inspection sample, 2 denotes a welded portion, 3 denotes a flaw inside a wall thickness, 4 denotes water for transmitting the ultrasonic wave, 5 denotes a linear array probe, 6 denotes a transducer element group for wave transmission, 7 denotes a transducer element group for wave reception, 8 denotes a wave transmission beam, and 9 denotes a portion of the ultrasonic wave directed from the flaw to the group of transducer elements for wave reception (hereinafter referred to as wave reception beam), respectively. Each line drawn at intermediate portions of the wave transmission beam 8 and the wave reception beam 9 indicates a scanning line, respectively.

The linear array probe 5 has the size sufficient to allow direct irradiation of the ultrasonic wave transmitted from the group of transducer elements closer to the welded portion 2 (left side shown in FIG. 1) from the outer surface of the welded portion of the steel pipe, and irradiation of the ultrasonic wave transmitted from the group of transducer elements at the remote side from the welded portion to the outer surface of the welded portion of the steel pipe after the single reflection at the inner surface of the steel pipe. It is structured to have the incident angle with respect to the outer circumferential surface of the steel pipe such that the wave transmission beam vertically transmitted from the center enters from the outer surface side of the steel pipe as the shear wave at the refraction angle of 45°, and further enters to the end of the welded portion at the inner surface side of the steel pipe (0.5 skip).

The ultrasonic beam from the group of transducer elements 6 for wave transmission is slightly deflected to the center axis side of the array probe in accordance with the outer diameter of the steel pipe such that the refraction angle becomes 45°, and the delay time is set for each of the transducer elements so as to focus at the position across the welded portion 2. Likewise, the group of transducer elements 7 for wave reception is selected to receive the reflection echo from the flaw 3 as the single reflection wave at the inner surface side. The beam is slightly deflected to the center axis of the array probe in accordance with the outer diameter of the steel pipe such that the refraction angle becomes 45°, and the delay time is set for each of the transducer elements so as to focus at the position across the welded portion 2. The refraction angle is set to 45°, however, it may be set to the angle in the range from approximately 30° to 70° where the shear wave is allowed to perform the flaw detection. In consideration with the angle-dependence of the sound pressure reflectance upon reflection of the shear wave at the flaw and the inner surface, it is preferable to set the refraction angle to be in the range from approximately 35° to 55° corresponding to the total reflection. The refraction angle may further be in the range from 40° to 50° in consideration with the stability.

As described above, each location, number, and refraction angle of the group of transducer elements for the wave transmission beam and the wave reception beam may be set for focusing in accordance with the welded portion, and the positional relationship of those groups may be set to receive the wave reflecting from the flaw. This makes it possible to detect the reflection from the minute flaw inside the wall thickness.

FIGS. 2A to 2D show the example of procedure for scanning the welded portion from the inner surface to the outer surface of the steel pipe. In step 1 upon start of the scanning, the focus position (focal position) is set to the welded portion at the inner surface side of the steel pipe using the group of transducer elements around the center of the linear array probe for performing the flaw detection through 0.5 skip reflection method. At this time, the wave transmission and the wave reception are performed using the same transducer element group. In step 2, the group of transducer elements for the wave transmission is shifted to the side of the welded portion, and the group of transducer elements for the wave reception is shifted remotely from the welded portion to set the focus position slightly above the inner surface side of the steel pipe (outer surface side of the steel pipe) so as to detect the flaw inside the wall thickness slightly above the welded portion at the inner surface side of the steel pipe through the tandem flaw detection.

In step 3, the group of transducer elements for the wave transmission is shifted to the welded portion and the group of transducer elements for the wave reception is shifted in the direction opposite the welded portion such that the flaw detection position on the welded portion is moved toward the outer surface side of the steel pipe for the flaw detection. The drawing shows steps 2 and 3 only. Actually, however, the number of the group of transducer elements to be shifted is determined to have the ultrasonic beams partially overlapped for allowing the efficient flaw detection without missing (leak) nor overlapping the flaw. In the last step 4 indicating the end of the scanning, the group of transducer elements at the position remotely from the welded portion is used to detect the flaw through the 1.0 skip reflection method on the welded portion at the outer surface side. As the processes in steps 1 to 4 are repeatedly executed, and the relative position of the steel pipe and the linear array probe is mechanically scanned in the pipe axial direction, the entire length of the welded portion (from the outer surface side to the inner surface side) is subjected to the flaw detection.

Figure 3:
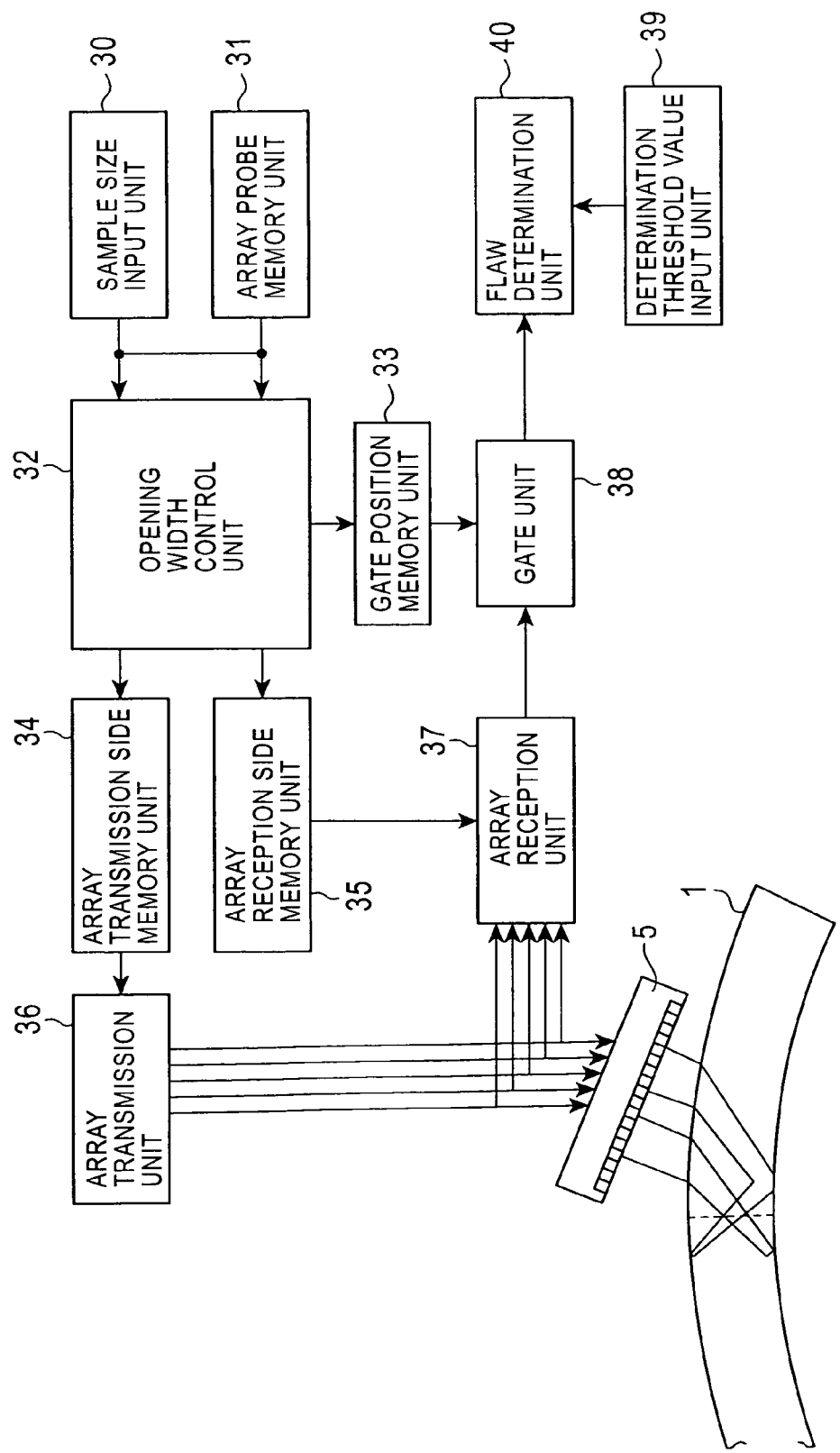
FIG. 3 is a functional arrangement example of an ultrasonic flaw detection apparatus according to the present invention.

FIG. 3 shows an example of the structure of the ultrasonic flaw detection apparatus according to the present invention. A sample size input unit 30 receives inputs of an outer diameter and a wall thickness of the steel pipe subjected to the flaw detection from the operator or the processing computer. An array probe memory unit 31 stores the frequency, the transducer element pitch, and the number of the transducer elements of the array probe 5.

An aperture control unit 32 calculates the position of the wave transmission array probe, the number of the wave transmission scanning lines, and the path of the wave transmission beam for the scanning lines in accordance with the size of the steel pipe and the specification of the array probe. Then the focus distance and the deflection angle are obtained on the respective paths. The obtained focus distance and the ultrasonic frequency are substituted in the formula (1) to obtain the aperture such that the beam width is brought into the predetermined range. The applicable beam width is in the range from 0.5 to 2.5 mm, preferably from 0.7 mm to 2.5 mm, and more preferably from 1.0 to 2.0 mm.

The aperture is divided by the transducer element pitch to obtain the number of the transducer elements of the wave transmission transducer element group for the respective scanning lines. The position of the wave transmission transducer element group is determined based on the scanning line position and the number of the transducer elements. The delay time for each of the transducer elements for the respective scanning lines is calculated. The above-determined values will be referred to as an array transmission law.

The aperture control unit 32 calculates the position of the array probe, the number of the wave reception scanning lines, and the wave reception beam path for the scanning line in accordance with the size of the steel pipe and the specification of the array probe. Then the focus distance and the deflection angle on the respective paths are obtained. The obtained focus distance and the ultrasonic frequency are substituted in the formula (1) to obtain the aperture so as to bring the beam width into the predetermined range. Likewise the wave transmission, the applicable beam width for the wave reception is in the range from 0.5 to 2.5 mm, preferably from 0.7 mm to 2.5 mm, and more preferably from 1.0 to 2.0 mm.

The aperture is divided by the transducer element pitch to obtain the number of the transducer elements of the wave reception transducer element group for the respective scanning lines. The position of the wave reception transducer element group is determined based on the scanning line position and the number of the transducer elements. The delay time for each of the transducer elements for the respective scanning lines is calculated. The above-determined values will be referred to as an array reception law. Based on the beam path calculated by the aperture control unit 32, the gate position for detecting the flaw is determined to be stored in the gate position memory unit 33.

The array reception law may be determined based on the previously obtained array transmission law. Conversely, the array transmission law may be determined based on the, previously obtained array reception law. The thus determined array transmission law and the array reception law are stored in an array transmission law memory unit 34 and an array reception law memory unit 35, respectively so as to be used for executing the transmission/reception control to be described below.

An array transmission unit 36 selects the wave transmission transducer element group based on the array transmission law stored in the array transmission law memory unit 34, and generates a transmission pulse by setting the delay time for the respective elements. An array reception unit 37 selects the wave reception transducer element group based on the array reception law stored in the array reception law memory unit 35, sets the delay time for the respective elements to add the signal and obtains the flaw detection waveform. A gate unit 38 extracts the signal at the gate position stored in the gate memory unit 33.

A flaw determination unit 40 compares a flaw determination threshold value input to a determination threshold value input unit 39 with the signal intensity in the gate. If the signal intensity is equal to or larger than the threshold value, it is determined to have the flaw. Upon the end of the flaw detection on the single scanning line, the group of transducer elements for the next wave transmission is selected based on the array transmission law stored in the array transmission law memory unit 34 to conduct the flaw detection as described above repeatedly. It may be determined to have the flaw if the signal intensity equal to or larger than the threshold value is detected plural times.

The procedure for controlling the group of transducer elements for scanning the beam in the thickness direction of the welded surface will be described using the ultrasonic flaw detection apparatus. Specifically, the respective transducer element groups for the wave transmission/reception, the number of the transducer elements, the deflection angle, and the focus distance may be determined in the following procedures. It is assumed that each width of the group of transducer elements for the wave transmission and the wave reception is obtained by the focusing coefficient for providing the required sensitivity so as to have the refraction angle constant. This will be described referring to FIGS. 1 and 4A and 4B. The following descriptions a), b) and g) correspond with the aforementioned sections 1), 2) and 3), the explanation, thus, will be briefly made hereinafter.

a) The position of the linear array probe is obtained such that the beam transmitted from the transducer element at the center of the linear array probe vertically to the probe surface enters into the steel pipe as the shear wave at the predetermined refraction angle (for example the refraction angle of 45°) so as to enter into the welded portion at the inner surface side or the outer surface side of the steel pipe.

b) The incident point is geometrically determined such that the incident angle of the beam from the respective transducer elements to the outer surface of the steel pipe is kept constant or brought into the predetermined range, and the line (scanning line) which passes inside the steel pipe at the refraction angle of 45° is determined.

Each transducer element represents the one corresponding to the center of the wave transmission unit. The positional relationship between the wave transmission transducer element group and the incident point on the outer surface of the steel pipe is determined. The propagation path after incidence to the steel pipe, that is, reflection points on the inner surface, the outer surface, and the welded surface may be defined in accordance with the refraction angle.

c) The deflection angle of each of the scanning lines is calculated based on the positional relationship between the above incident point and each of the respective transducer elements.

d) The water equivalent traveling distance of each of the respective scanning lines and the path length inside the steel to the welded portion are calculated and converted with the sonic speed and the water equivalent traveling distance to obtain the underwater focus distance F.

e) The aperture D for each of the respective scanning lines is calculated in accordance with the required beam width d through the formula (1), and the calculated aperture D is divided by the transducer element pitch and rounded off to provide the number n of the transducer elements of the group of transducer elements for the respective scanning lines (corresponding to the "number of transducer elements subjected to the simultaneous excitation"). The required beam width d denotes the beam diameter range to be applied for detecting the scattered-type penetrator having the minute flaws distributed in the wide range. The applicable beam is in the range from 0.5 to 2.5 mm, preferably, from 0.7 mm to 2.5, and more preferably from 1.0 to 2.0 mm.

f) The position of each of the respective transducer element groups which constitute the wave transmission unit is determined from the respective positions of the transducer elements for the scanning lines and the number n of the transducer elements.

g) The scanning line to be used for the flaw detection is determined based on the positional relationship of the scanning lines which intersect on the welded portion. The wave reception transducer element group which makes a pair with the wave transmission transducer element group is determined. The scanning lines which have propagated from opposite directions to intersect at the welded portion may form the pair. In the unnecessarily overlapped case at the same point on the welded portion relative to the required space resolution, the scanning lines may be decimated.

h) The number of the group of transducer elements, the focus distance, and the deflection angle are determined with respect to all the scanning lines for the flaw detection. Each delay time set for the respective transducer elements is calculated. The calculation method may be the same as the one disclosed in Patent Document 5 which has been filed for patent application by the inventors.

The basic calculation concept will be described referring to FIG. 5 and the formula hereinafter. The coordinate of the focus position {Xf, Yf} is obtained through the following equation having the center of the group of transducer elements as the origin of the coordinate, the focus distance referred to as F, and the deflection angle referred to as θ.

$$Xf = F \cdot \sin\theta, \quad Yf = -F \cdot \cos\theta$$

Figure 5:
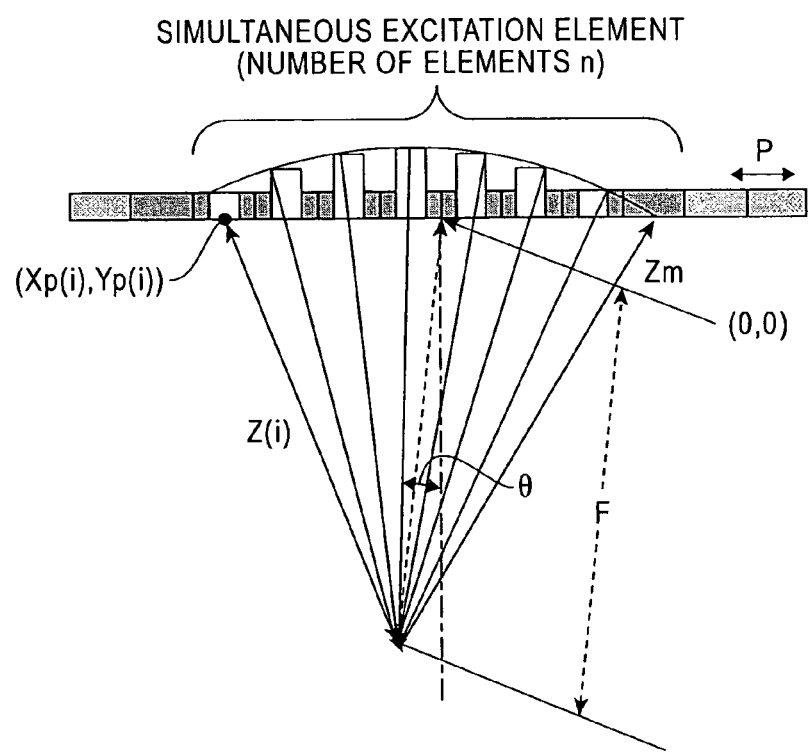
FIG. 5 is a view showing a calculation of the delay time applied to the respective transducer elements.

Then each coordinate of the respective transducer elements {Xp(i), Yp(i)} is obtained having the transducer element pitch defined as P, the number of the transducer elements of the group of transducer elements (corresponding to the "number of the transducer elements subjected to the simultaneous excitation" in claim 3, which is referred to as the "simultaneous excitation element" in FIG. 5) defined as n (n: even number).

$$Xp(i) = -n \cdot p/2 - p/2 + p \cdot i, \quad Yp(i) = 0 \, (i=1 \text{ to } n)$$

The distance Z(i) between the focus position and each of the respective transducer elements, and the maximum value Zm thereof are obtained through the following equations.

$$Z(i) = SQRT\{(Xf - Xp(i))^2 + (Yf - Yp(i))^2\} \, (i=1 \text{ to } n)$$

$$Zm = \max\{Z(i)\} \, (i=1 \text{ to } n)$$

Finally, the delay time $\Delta t(i)$ is obtained through the following equation.

$$\Delta i\, t(i) = (Zm - Z(i))/C \, (i=1 \text{ to } n)$$

where C denotes the sonic speed.

The aforementioned equations indicate the basic concept of the calculation, and the center of the group of transducer elements for the respective scanning lines does not have to be the origin of the coordinate. In the description, the number n of the transducer elements is even, but it may be an odd number. The aforementioned equations are partially changed to allow the use of the odd number. In the actual calculation, each coordinate of the array probe element is preliminarily set such that the coordinate of the focus position is obtained in accordance with the focus distance and the deflection angle. Then the distance Z(i) between the focus position and each of the respective transducer elements may be obtained.

FIGS. 4A and 4B show examples of the thus determined scanning line, and exemplary results of calculating the flaw detection condition with respect to the representative points of the scanning line. It is assumed in the example that the steel pipe with the outer diameter of 558.8 mm and thickness of 25.4 mm is subjected to the flaw detection at the water equivalent traveling distance 20 mm from the center at the refraction angle of 45° using the linear array probe which includes 160 elements (transducer elements) at each pitch of 0.5 mm. The numbers from 1 to 160 are designated to the transducer elements from the closest side to the remote side.

The focus distance at the respective transducer element positions may be obtained as shown in Table of FIG. 4B. Based on the obtained focus distance, the curvature of the acoustic lens for focusing in the pipe axial direction of the pipe may be determined. As it is well known, the curvature r of the acoustic lens may be calculated through the following equation.

$$r = \{1 - (C2/C1)\}F \tag{3}$$

The scanning lines A, B and C are shown by a two-dot chain line, a broken line, and a chain line, respectively. Both sides of each of the scanning lines A, B and C are kept blank for easy comprehension. Each black mark indicating the probe represents the group of transducer elements for transmitting/receiving the scanning lines.

Figure 6A:
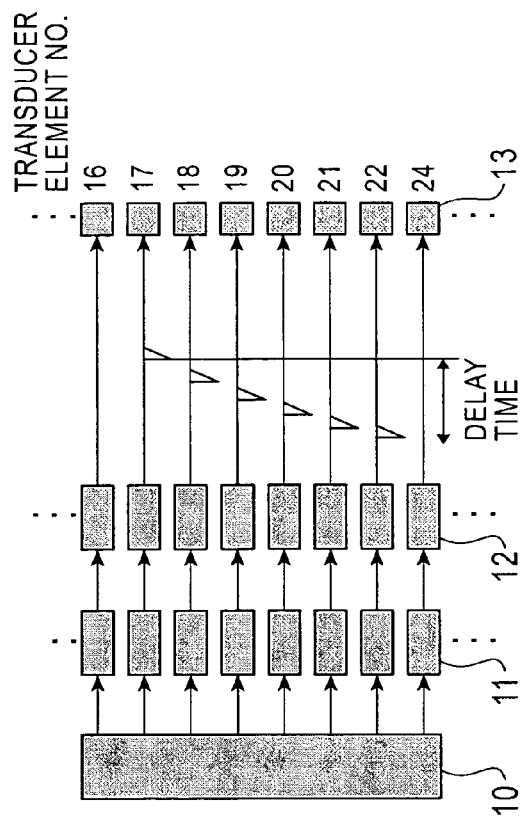
FIGS. 6A and 6B show the calculation results of the delay time with respect to the scanning line A and the principle of the wave transmission.
Figure 6B:
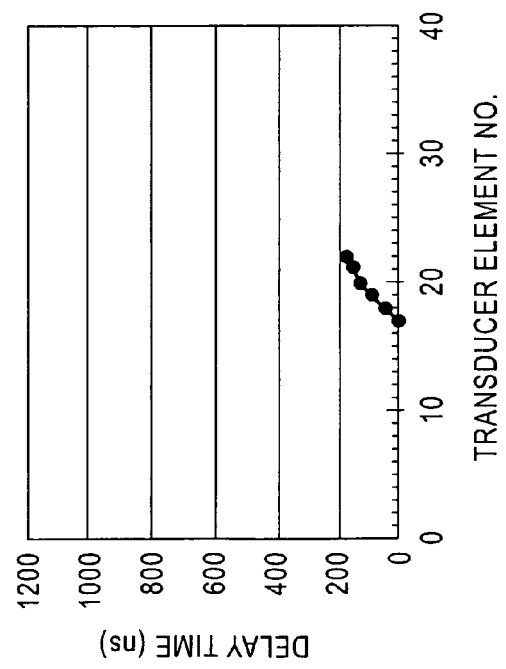

FIGS. 6A and 6B show calculation results of the delay time for the scanning line A shown in FIG. 4A, and the principle of the wave transmission. Referring to the drawing, a reference numeral 10 denotes a flaw detection condition calculation unit for calculating with respect to the sections 1) to 8), a reference numeral 11 denotes a delay time set unit for determining the wave transmission timing of the wave transmission pulse based on the calculated flaw detection condition, 12 denotes a pulsar, and 13 denotes each transducer element of the linear array probe 5. Referring to the drawing, the transducer elements designated with the numbers from 17 to 22 are only selected. The transducer element with the no. 17 is excited first, and the transducer elements from nos. 18 to 22 are sequentially excited with the time lag for forming the wave transmission beam corresponding to the scanning line A.

Figure 7B:
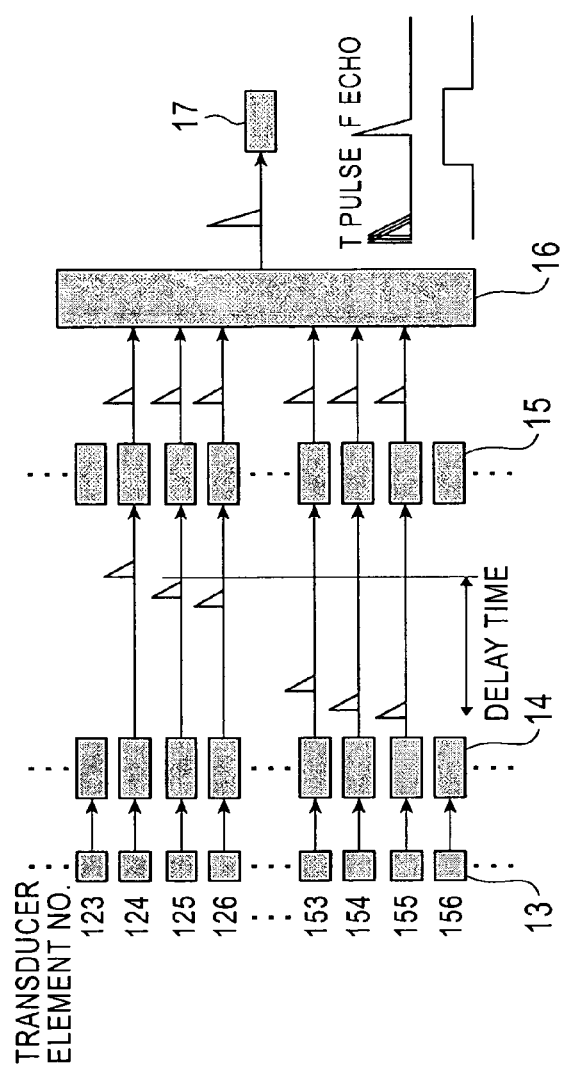
FIGS. 7A and 7B show the calculation results of the delay time with respect to the scanning line C and the principle of the wave reception.
Figure 7A:
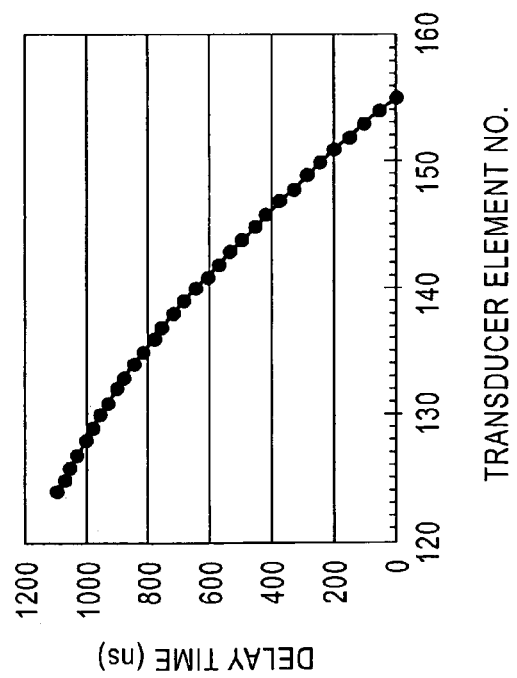

FIGS. 7A and 7B show calculation results of the delay time for the scanning line C shown in FIG. 4A and the principle of the wave reception. Referring to the drawing, a reference numeral 13 denotes each of the respective transducer elements of the linear array probe, 14 denotes a reception amplifier, 15 denotes a delay time set unit, 16 denotes a synthesizing unit, and 17 denotes a gate evaluation unit. In the drawing, the transducer elements with the nos. from 124 to 155 are only selected. The echo from the flaw is first irradiated to the transducer element no. 124, and is further received by the respective transducer elements from nos. 125 to 155 sequentially with the time lag. The delay time set unit 15 corrects the time lag to align the phase. The synthesizing unit 16 performs the synthesizing to enlarge the echo by the focus effect.

Then the wave reception corresponding to the scanning line C is performed. Thereafter, existence of the flaw echo (F echo in the drawing) is determined by the gate evaluation unit 17 in the time zone (gate) set from the wave transmission pulse (T pulse in the drawing) to the distance in accordance with the beam path length for conducting the flaw detection. The delay time set unit 15, the synthesizing unit 16, and the gate evaluation unit 17 may be realized by the software subsequent to A/D conversion immediately after the output from the reception amplifier 14 to store the signal in the memory.

In the example, the flaw detection calculation is sequentially performed after determining the incident points of the respective scanning lines as the above section 2}onward. However, the calculation is not limited to the aforementioned process. For example, the focus position is determined first, and then the path corresponding to the shortest propagation time to the focus position may be searched for each of the respective transducer elements.

EXAMPLE 2

Figure 8:
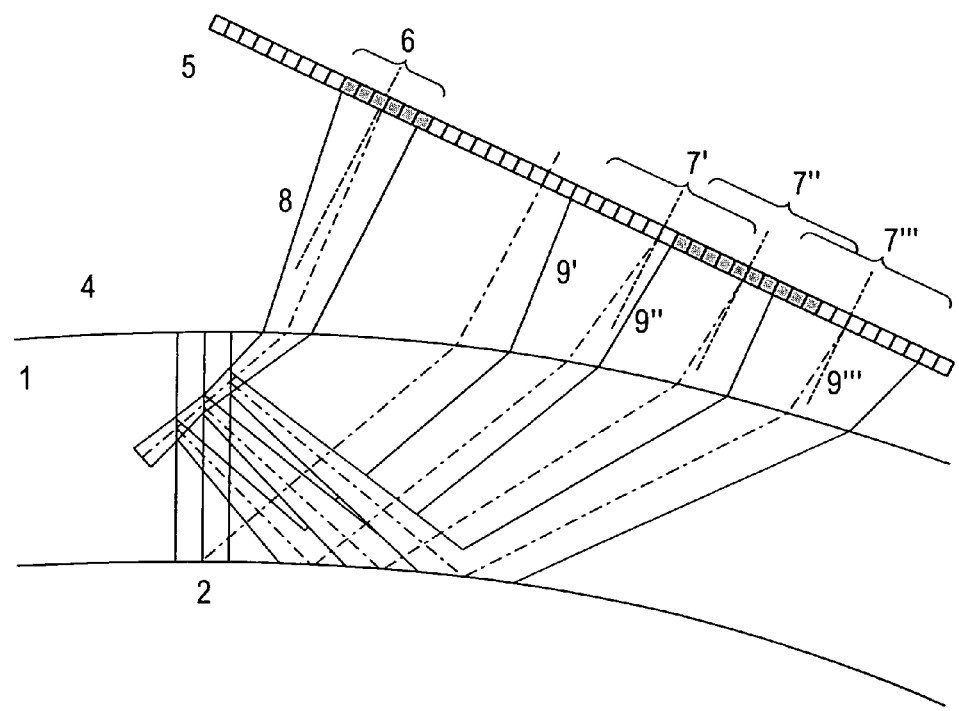
FIG. 8 is an explanatory view of Example 2 of the present invention.

Example 2 according to the present invention will be described. FIG. 8 shows Example 2 indicating setting and procedure for the flaw detection in step 3 shown in FIG. 2C. Reference numerals 7' to 7''' denote the group of transducer elements for wave reception, 9' to 9''' denote the wave reception beams. In this example, the wave transmission beam 6 is transmitted from the group of transducer elements 5 for wave transmission, and is received by the group of transducer elements 7' for wave reception. Then the transmission beam 6 is transmitted from the group of transducer elements 5 for wave transmission so as to be received by the group of transducer elements 7'' for wave reception. The transmission beam 6 is transmitted from the group of transducer elements 5 for the wave transmission so as to be received by the group of transducer elements 7''' for the wave reception. The above-described procedure having arbitrary scanning lines intersecting at the welded portion allows detection without missing the flaw irrespective of lateral displacement owing to incapability of identifying the welded position, low positioning accuracy, and oscillation.

EXAMPLE 3

Figure 9:
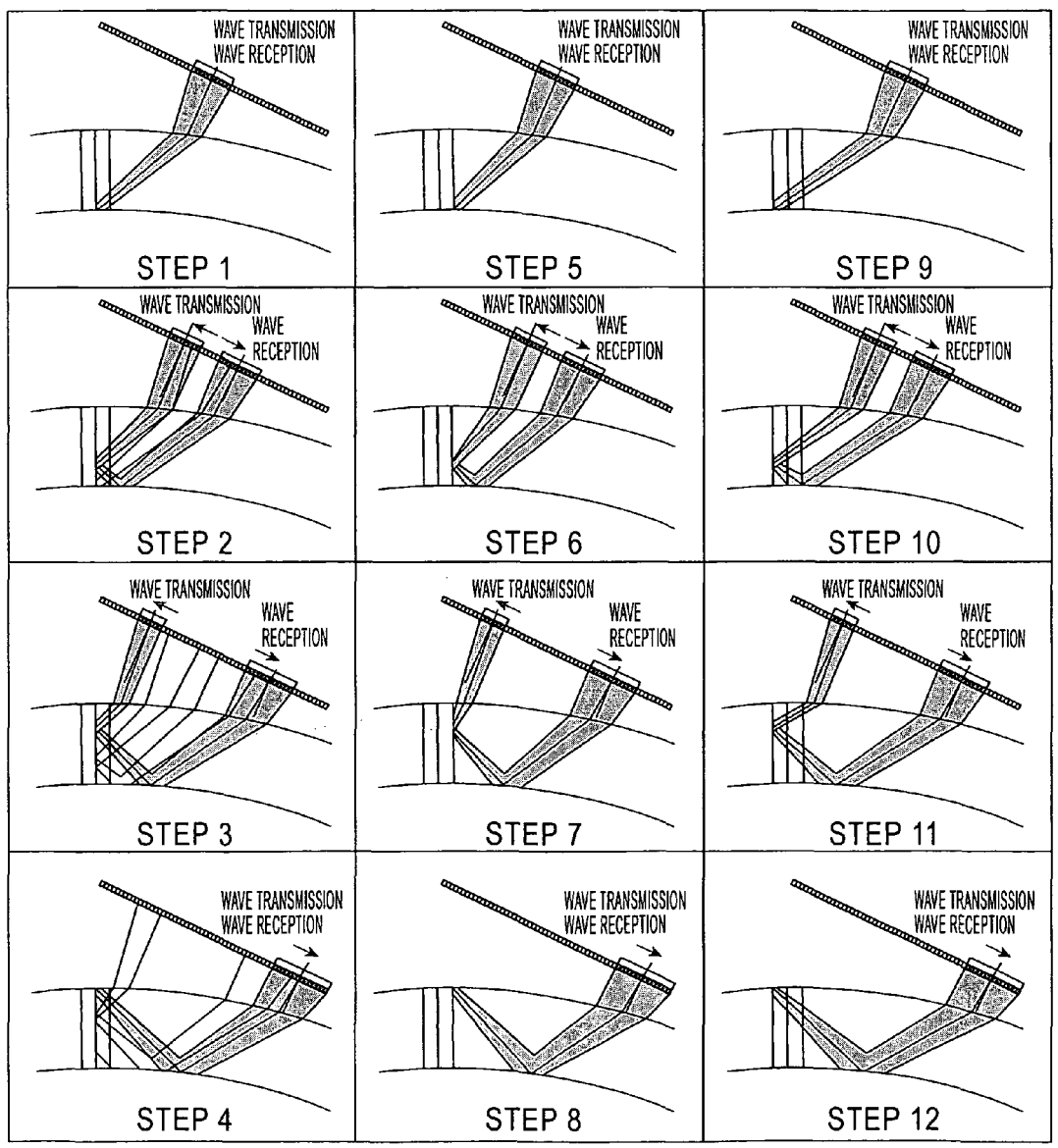
FIG. 9 is an explanatory view of Example 3 of the present invention.

Example 3 of the present invention will be described hereinafter. FIG. 9 shows Example 3 according to the present invention. In Example 3, the wall thickness of the portion of the pipe in the circumferential direction is entirely subjected to the flaw detection in steps 1 to 4 as shown in FIGS. 2A to 2D, the portions to the front (right side in the drawing) and to the rear (left side in the drawing) of the scanning position are subjected to the flaw detection in steps 5 to 8, and steps 9 to 12, respectively.

The above-described procedure having arbitrary scanning lines intersecting at the welded portion allows detection without missing the flaw irrespective of lateral displacement owing to incapability of identifying the welded position, low positioning accuracy, and oscillation. Referring to FIG. 9, scanning lines intersect at three positions in the circumferential direction of the pipe. However, such number is not limited to the value as described above. The intersecting positions of the scanning lines may be shifted by displacing the position of the group of transducer elements for the transmission or reception, or changing the deflection angle.

EXAMPLE 4

Figure 10:
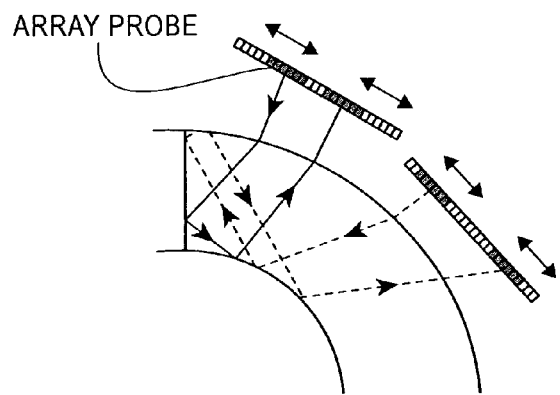
FIG. 10 is an explanatory view of Example 4 of the present invention.

Example 4 according to the present invention will be described. In Example 1, the single array probe is used for scanning the entire region of the welded surface in the thickness direction (radial direction of the pipe). In Example 4, plural array probes each having the wave transmission unit and the wave reception unit are arranged in the circumferential direction. Each of the plural array probes serves to scan the divided portion of the welded surface in the thickness direction (radial direction of the pipe) as shown in FIG. 10.

In the example, two array probes are employed, one of which at the left side in the drawing functions in detecting the flaw from the inner surface to the center of the wall thickness, and the other side of which at the right side functions in detecting the flaw from the center of the wall thickness to the outer surface. In the case where the single array probe is employed to detect the flaw from the inner surface to the outer surface as shown in FIGS. 2A to 2D, the long array probe is required for detecting the material with large wall thickness. When the group of transducer elements for the wave transmission or the wave reception is moved to the end of the array probe, the deflection angle becomes too large, thus deteriorating the sensitivity.

Meanwhile in the present example, plural array probes are employed to cover the divided wall thickness portions. The array probe does not have to be long, thus suppressing deterioration in the sensitivity while preventing increase in the deflection angle. In the case where the steel pipe with thickness of 25 mm is subjected to the flaw detection in Example 1, the array probe is required to have the length of 88 mm. The deflection angle when the group of transducer elements is set to the outermost end is set to be ±5.9°.

Supposing that the width and the frequency of the single element of the array probe are set to 0.95 mm and 10 MHz, respectively, the sensitivity is deteriorated due to deflection to 17.4 dB. Upon compensation of the sensitivity by increasing the reception gain, the electric noise will be increased as well, thus failing to increase the S/N ratio. Meanwhile, in the present example, the array probe may have the length of only 60 mm, and the deflection angle of the group of transducer elements at the outermost end becomes ±3.4°, resulting in the sensitivity drop to 5 dB. This makes it possible to suppress increase in the electric noise even if the sensitivity is corrected by increasing the reception gain.

EXAMPLE 5

Figure 11:
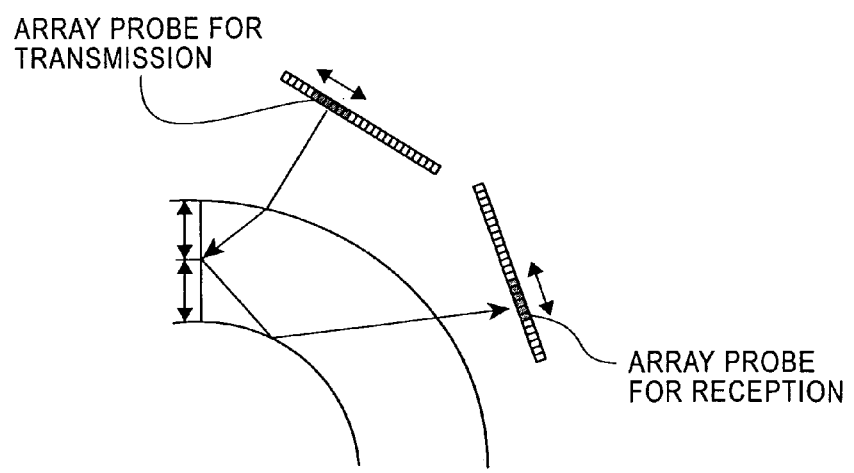
FIG. 11 is an explanatory view of Example 5 of the present invention.

Example 5 according to the present invention will be described. In Examples 1 and 4, the single array probe includes the wave transmission unit and the wave reception unit. Example 5 employs plural array probes each containing one of the wave transmission unit and the wave reception unit, respectively as shown in FIG. 11. The wave transmission/reception may be performed by the respective optimized array probes, thus improving the sensitivity. The angle may be set optimally to the respective steel pipes to reduce the deflection angle, thus suppressing deterioration in the sensitivity.

EXAMPLE 6

Figure 12:
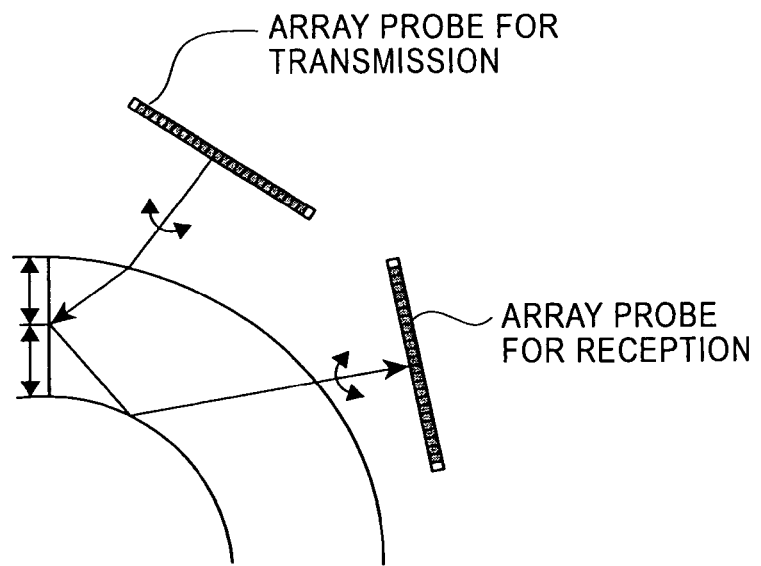
FIG. 12 is an explanatory view of Example 6 of the present invention.

In Examples 1 to 5, the wave transmission unit and the wave reception unit are formed using the group of transducer elements as a part of the array probe so as to scan the welded surface while moving the wave transmission unit and the wave reception unit. In Example 6, plural array probes for wave transmission and wave reception are separately disposed as shown in FIG. 12 such that all the group of transducer elements of the array probe are used for wave transmission/reception. As the intersect position between the wave transmission beam and the wave reception beam is set, the deflection angle is changed for scanning the welded surface. In this way, as all the elements of the array probe may be used as the group of transducer elements, the opening is expanded to increase the focusing coefficient. In the case where the array probe position is fixed, the relationship between the wave transmission beam and the wave reception beam does not become the mirror reflection with respect to the welded line. For this, the position of the wave transmission array probe or the wave reception array probe may be mechanically moved simultaneously with the change in the deflection angle such that the relationship between the wave transmission beam and the wave reception beam becomes the mirror reflection with respect to the welded line.

EXAMPLE 7

Figure 13:
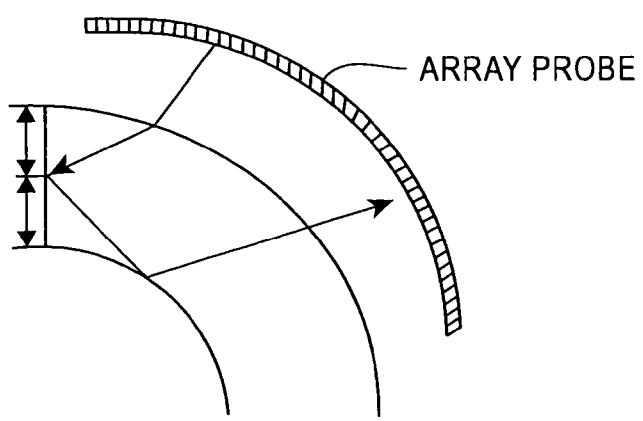
FIG. 13 is an explanatory view of Example 7 of the present invention.

Example 7 according to the present invention will be described. In Example 7, the array probe is formed into the configuration in accordance with the curvature of the pipe as shown in FIG. 13. Unlike Examples 1 to 6, the aforementioned structure allows easy scanning while keeping the deflection angle and refraction angle constant without performing the complicated calculation of the deflection angle like the case of the linear array probe irrespective of the change in the incident position of the transmission and reception. This may suppress variation in the sensitivity.

Each structure described in Example 4 to 7 is not limited to the one employed as the single structure. For example, the welded surface is divided into the inner surface side and the outer surface side so as to combine the inner surface side formed into the structure according to Example 4 with the outer surface side formed into the structure according to Example 5. Alternatively, the array probe with the curvature of the pipe according to Example 7 combined with the structure for controlling the refraction angle and the delay time may be employed.

INDUSTRIAL APPLICABILITY

According to the present invention, the scattered-type penetrator having flaws each with the micro diameter dispersed in the wide region may be detected to improve the welding process without generating the minute flaw which influences the mechanical characteristics of the welded portion of the welded steel pipe, and to detect the flaw in the manufacturing step so as not to be missed. This makes it possible to markedly improve quality of the welded steel pipe to allow the usage of the structure under the more severe service conditions as ever before.

What is claimed is:

1. An ultrasonic flaw detection apparatus for a pipe comprising:
  a wave transmission unit for transmitting an ultrasonic wave to a welded surface of a welded portion of the pipe in a pipe axial direction so that a beam width of the ultrasonic wave is within a range from 0.5 mm to 2.5 mm; and
  a wave reception unit configured to receive partly or entirely a reflection wave reflected from penetrators dispersed in the beam area at the welded surface,
  wherein the wave transmission unit and the wave reception unit are provided with transmission/reception units comprising different groups of transducer elements on at least one array probe arranged in a circumferential direction of the pipe, and the wave transmission unit and the wave reception unit are configured to detect the presence of penetrators.

2. The ultrasonic flaw detection apparatus for a pipe according to claim 1, further comprising a control unit for controlling an aperture width of the ultrasonic wave for transmission such that the beam width of the ultrasonic beam is held in the range.

3. The ultrasonic flaw detection apparatus for a pipe according to claim 2, wherein the control unit controls the aperture width of the ultrasonic wave by a number of transducer elements to be simultaneously excited.

4. The ultrasonic flaw detection apparatus for a pipe according to claim 2, wherein:
  the wave transmission unit transmits the ultrasonic wave to the welded surface of the welded portion of the pipe in the pipe axial direction and an inner surface of the pipe so that the ultrasonic wave is incident at an angle ranging from 33.2° to 56.8°, respectively;
  the wave reception unit receives partly or entirely the reflection wave in a direction within a range from −12° to 16° with respect to a mirror reflection direction on the welded surface; and
  the control unit scans the pipe in a thickness direction by carrying out a control to change the group of transducer elements corresponding to the wave transmission unit and the wave reception unit on the array probe or to change an angle of the array probe, and controlling an incident angle of the ultrasonic wave to the pipe in the respective transmitting wave and receiving waves so that the angles of incidence to the welded surface and the inner surface and the angle of the reflection wave on the welded surface are kept within the ranges as to the transmitted wave and the received wave, respectively.

5. The ultrasonic flaw detection apparatus for a pipe according to claim 4, wherein the control unit controls the incident angle and the focus position to the pipe by shifting a timing for the wave transmission and/or the wave reception with respect to each of the transducer elements in the group of transducer elements so that the incident angle to the welded surface and the inner surface, and the angle of the reflecting wave on the welded surface are kept within the defined ranges, respectively.

6. The ultrasonic flaw detection apparatus for a pipe according to claim 4, wherein the incident angle of at least one of the ultrasonic wave at the transmission side and the ultrasonic wave at the reception side to the pipe is kept to a predetermined angle.

7. The ultrasonic flaw detection apparatus for a pipe according to claim 4, wherein the control unit controls at least one of the wave transmission and the wave reception with respect to the respective transducer elements so that the incident angle of the ultrasonic wave to the pipe is made to a predetermined angle.

8. The ultrasonic flaw detection apparatus for a pipe according to claim 4, wherein:
  the transmission unit and the reception unit of the transmission/reception unit comprise different array probes; and
  the control unit changes deflection angles of the wave transmission beam and the wave reception beam from the respective array probes.

9. The ultrasonic flaw detection apparatus for a pipe according to claim 4, wherein the control unit changes the incident angle and the focus position of the ultrasonic wave to the pipe upon the wave transmission or the wave reception so that scanning lines of the wave transmission beam intersect the wave reception beam at a plurality of positions in the circumferential direction of the pipe.

10. The ultrasonic flaw detection apparatus for a pipe according to claim 1, wherein the wave transmission unit transmits the ultrasonic wave having a focusing coefficient of from −13 dB to 28 dB, the focusing coefficient indicates increase in an acoustic pressure at a focus position.

11. The ultrasonic flaw detection apparatus for a pipe according to claim 1, wherein the array probe has the group of transducer elements with a curvature so that they are disposed along the circumferential direction of the pipe.

12. The ultrasonic flaw detection apparatus for a pipe according to claim 1, wherein the array probe includes an acoustic lens for focusing the wave transmission beam and the wave reception beam to the pipe axial direction of the pipe, and a focus distance of the acoustic lens is set shorter as it is nearer to the welded portion and longer as it is farther from the welded portion.

13. The ultrasonic flaw detection apparatus for a pipe according to claim 1, wherein the transmission/reception unit comprises a plurality of array probes as well as includes a wave transmission unit and a wave reception unit on each array probe.

14. The ultrasonic flaw detection apparatus for a pipe according to claim 1, wherein the transmission unit and the reception unit of the transmission/reception unit comprise different array probes.

15. The ultrasonic flaw detection apparatus for a pipe according to claim 1, wherein the wave transmission unit transmits the ultrasonic wave having a focusing coefficient of from −13 dB to 28 dB, the focusing coefficient indicates increase in an acoustic pressure at a focus position, wherein:
the wave transmission unit transmits the ultrasonic waves to the welded surface of the welded portion of the pipe in the pipe axial direction and an inner surface of the pipe so that the ultrasonic wave is incident at an angle ranging from 33.2° to 56.8°, respectively;
the wave reception unit receives partly or entirely the reflection wave in a direction within a range from −12° to 16° with respect to a mirror reflection direction on the welded surface; and
the control unit scans the pipe in a thickness direction by carrying out a control to change the group of transducer elements corresponding to the wave transmission unit and the wave reception unit on the array probe or to change an angle of the array probe, and controlling an incident angle of the ultrasonic wave to the pipe in the respective transmitting wave and receiving waves so that the angles of incidence to the welded surface and the inner surface and the angle of the reflection wave on the welded surface are kept within the ranges as to the transmitted wave and the received wave, respectively, and
wherein the control unit controls the incident angle and the focus position to the pipe by shifting a timing for the wave transmission and/or the wave reception with respect to each of the transducer elements in the group of transducer elements so that the incident angle to the welded surface and the inner surface, and the angle of the reflecting wave on the welded surface are kept within the defined ranges, respectively.

16. An ultrasonic flaw detection method for a pipe, wherein the ultrasonic flaw detection method uses an ultrasonic flaw detection apparatus for a pipe comprising a wave transmission unit and a wave reception unit composed of different groups of transducer elements on at least one array probe arranged in a circumferential direction of the pipe, the method comprising
transmitting the ultrasonic wave to a welded surface of a welded portion of the pipe in an axial direction such that a beam width is within a range from 0.5 mm to 2.5 mm, receiving a wave reflected from penetrators dispersed in the beam area at the welded surface, and determining whether the penetrators are present at the welded surface.

17. The ultrasonic flaw detection method for a pipe according to claim 16, wherein an aperture width of the ultrasonic wave used for the wave transmission is controlled such that the beam width of the ultrasonic beam to the welded surface is kept in the range.

18. The ultrasonic flaw detection method for a pipe according to claim 17, wherein the aperture width of the ultrasonic wave is controlled by a number of the transducer elements in the group of transducer elements to be simultaneously excited.

19. The ultrasonic flaw detection method for a pipe according to claim 16, wherein the ultrasonic wave having a focusing coefficient of from −13 dB to 28 dB is transmitted, the focusing coefficient indicating an increase in an acoustic pressure at a focus position.

20. The ultrasonic flaw detection method for a pipe according to claim 16, wherein:
the ultrasonic wave is transmitted from the wave transmission unit to the welded surface of the welded portion of the pipe in the pipe axial direction and an inner surface of the pipe so that incident angles are within a range from 33.2° to 56.8°, respectively;
at least a portion of a reflection wave reflected to a direction in a mirror reflection direction on the welded surface in a range from −12° to 16° is received by the wave reception unit: and
a scanning is performed in a direction of a thickness of the pipe under the control for changing the group of transducer elements corresponding to the wave transmission unit and the wave reception unit on the array probe or changing an angle of the array probe.

21. The ultrasonic flaw detection method for a pipe according to claim 16, wherein the incident angle to the pipe and the focus position are controlled by shifting a timing for the wave transmission and/or wave reception for the respective transducer elements in the group of transducer elements.

22. The ultrasonic flaw detection method for a pipe according to claim 16, wherein the incident angle of at least one of the ultrasonic wave at the wave transmission side and the ultrasonic wave at the wave reception side with respect to the pipe is kept to a predetermined angle.

23. The ultrasonic flaw detection method for a pipe according to claim 16, wherein an aperture width of the ultrasonic wave used for the wave transmission is controlled such that the beam width of the ultrasonic beam to the welded surface is kept in the range, wherein the aperture width of the ultrasonic wave is controlled by a number of the transducer elements in the group of transducer elements to be simultaneously excited, wherein the ultrasonic wave having a focusing coefficient of from −13 dB to 28 dB is transmitted, the focusing coefficient indicating an increase in an acoustic pressure at a focus position, wherein:
the ultrasonic wave is transmitted from the wave transmission unit to the welded surface of the welded portion of the pipe in the pipe axial direction and an inner surface of the pipe so that incident angles are within a range from 33.2° to 56.8°, respectively;
at least a portion of a reflection wave reflected to a direction in a mirror reflection direction on the welded surface in a range from −12° to 16° is received by the wave reception unit: and
a scanning is performed in a direction of a thickness of the pipe under the control for changing the group of transducer elements corresponding to the wave transmission unit and the wave reception unit on the array probe or changing an angle of the array probe, and wherein the incident angle to the pipe and the focus position are controlled by shifting a timing for the wave transmission and/or wave reception for the respective transducer elements in the group of transducer elements.

* * * * *